United States Patent
Bornzin et al.

(10) Patent No.: US 12,377,262 B2
(45) Date of Patent: Aug. 5, 2025

(54) METHOD AND IMPLANTABLE MEDICAL DEVICE FOR REDUCING DEFIBRILLATION IMPEDANCE

(71) Applicant: Pacesetter, Inc., Sylmar, CA (US)

(72) Inventors: Alexander R. Bornzin, Ventura, CA (US); Gene A. Bornzin, Los Angeles, CA (US); Zoltan Somogyi, Ventura, CA (US)

(73) Assignee: Pacesetter, Inc., Sylmar (CA)

( * ) Notice: Subject to any disclaimer, the term of this patent is extended or adjusted under 35 U.S.C. 154(b) by 368 days.

(21) Appl. No.: 17/804,041

(22) Filed: May 25, 2022

(65) Prior Publication Data

US 2023/0381500 A1    Nov. 30, 2023

(51) Int. Cl.
| | |
|---|---|
| *A61N 1/05* | (2006.01) |
| *A61B 17/34* | (2006.01) |
| *A61N 1/375* | (2006.01) |
| *A61N 1/39* | (2006.01) |

(52) U.S. Cl.
CPC ........ *A61N 1/0563* (2013.01); *A61B 17/3468* (2013.01); *A61N 1/0504* (2013.01); *A61N 1/0573* (2013.01); *A61N 1/3752* (2013.01); *A61N 1/3956* (2013.01)

(58) Field of Classification Search
None
See application file for complete search history.

(56) References Cited

U.S. PATENT DOCUMENTS

| | | | |
|---|---|---|---|
| 5,902,236 A | * | 5/1999 | Iversen .................. A61B 5/287 607/116 |
| 7,363,083 B2 | | 4/2008 | Bardy et al. |
| 8,483,841 B2 | | 7/2013 | Sanghera et al. |
| 9,079,035 B2 | | 7/2015 | Sanghera et al. |
| 10,137,295 B2 | | 11/2018 | Marshall et al. |
| 10,391,325 B2 | | 8/2019 | De Kock et al. |
| 10,661,073 B2 | | 5/2020 | Marshall et al. |
| 2007/0123940 A1 | * | 5/2007 | Dorr .................... A61N 1/3712 607/5 |
| 2016/0158567 A1 | * | 6/2016 | Marshall .............. A61N 1/0504 607/116 |
| 2016/0021392 A1 | | 7/2016 | Rosenberg et al. |
| 2016/0213311 A1 | * | 7/2016 | Zhang ................ A61N 1/39622 |

(Continued)

FOREIGN PATENT DOCUMENTS

| | | |
|---|---|---|
| EP | 3976167 A1 | 4/2022 |
| WO | 2020243534 A1 | 12/2020 |
| WO | 2022009100 A2 | 1/2022 |

OTHER PUBLICATIONS

U.S. Appl. No. 63/049,561, filed Jul. 8, 2020 (18 pages).

(Continued)

*Primary Examiner* — Mallika D Fairchild
(74) *Attorney, Agent, or Firm* — Dean D. Small; The Small Patent Law Group, LLC

(57) ABSTRACT

Methods and implantable medical devices are provided that include a lead configured to be operably coupled to a pulse generator and subcutaneously implanted within a patient. The lead includes an electrode configured to receive electrical power from the pulse generator and to deliver high-voltage shocks for defibrillation therapy. The electrode has an oblong cross-sectional shape with a major dimension that is at least 10 French (F).

19 Claims, 9 Drawing Sheets

(56) References Cited

U.S. PATENT DOCUMENTS

| | | | |
|---|---|---|---|
| 2017/0319864 A1* | 11/2017 | De Kock | A61N 1/0563 |
| 2018/0272138 A1* | 9/2018 | Tahmasian | A61N 1/3758 |
| 2019/0336753 A1* | 11/2019 | Min | A61N 1/0587 |
| 2020/0376265 A1 | 12/2020 | Sanghera et al. | |
| 2020/0398044 A1 | 12/2020 | Sanghera et al. | |
| 2021/0370080 A1 | 12/2021 | Sanghera et al. | |
| 2021/0370081 A1 | 12/2021 | Sanghera et al. | |

OTHER PUBLICATIONS

U.S. Appl. No. 62/854,178, filed May 29, 2019 (91 pages).
User's manual, Emblem™ S-ICD, Electrode Delivery System, Model 4712. © 2017 Boston Scientific Corporation, <https://www.s-icd.es/content/dam/Manuals/us/current-rev-en/360244-001_EMBLEM_UM_en-USA_S.pdf>, (44 pages).
Frankel et al., "Impact of Body Mass Index on Safety and Efficacy of the Subcutaneous Implantable Cardioverter-Defibrillator", ACC: Clinical Electrophysiology 2018, vol. 4, No. 5: 652-659, (8 pages).
Quast et al., "A novel tool to evaluate the implant position and predict defibrillation success of the subcutaneous implantable cardioverter-defibrillator: The PRAETORIAN score", Heart Rhythm 2019, 16: 403-410, (8 pages).
Amin et al, "Factors associated with high-voltage impedance and subcutaneous implantable defibrillator ventricular fibrillation conversion success", Circ Arrhythm Electrophysiol 2019, (10 pages).
Heist et al, "Determinants of subcutaneous implantable cardioverter-defibrillator efficacy: a computer modeling study", JACC Clin Electrophysiol 2017, 3:405-414, (10 pages).

* cited by examiner

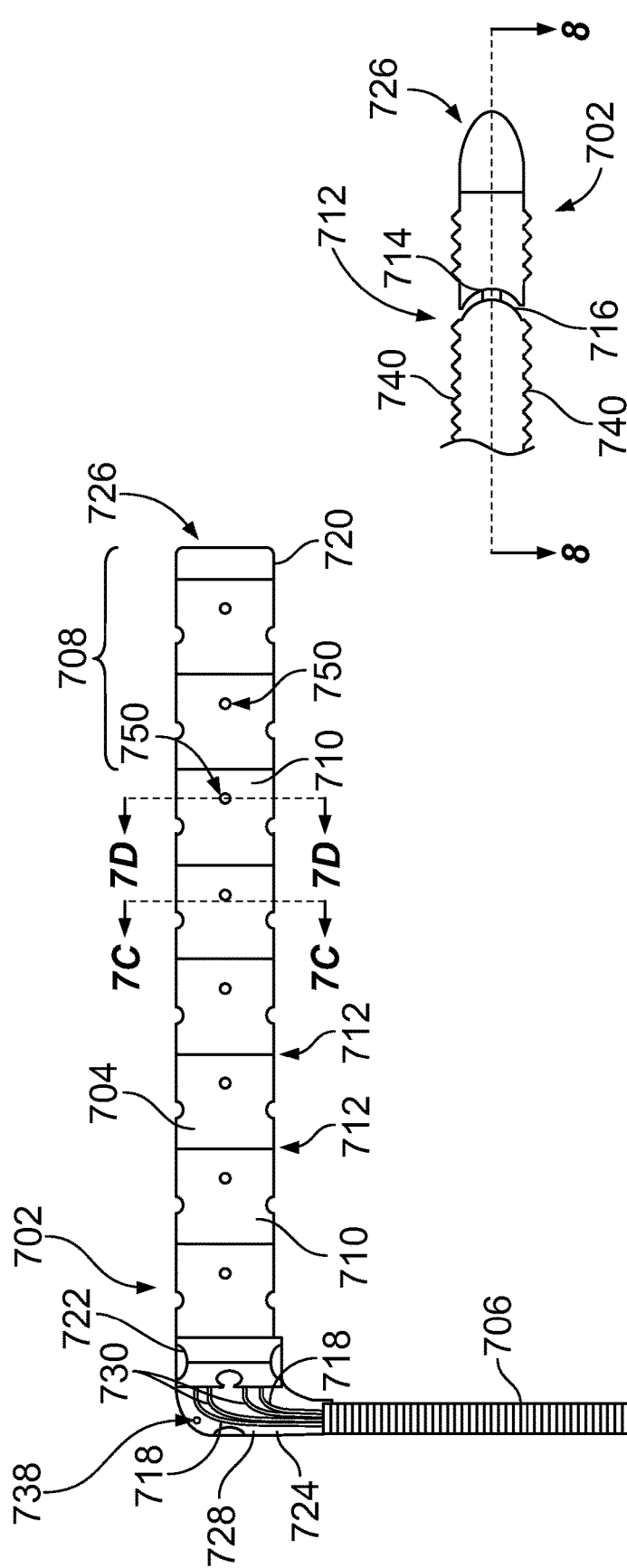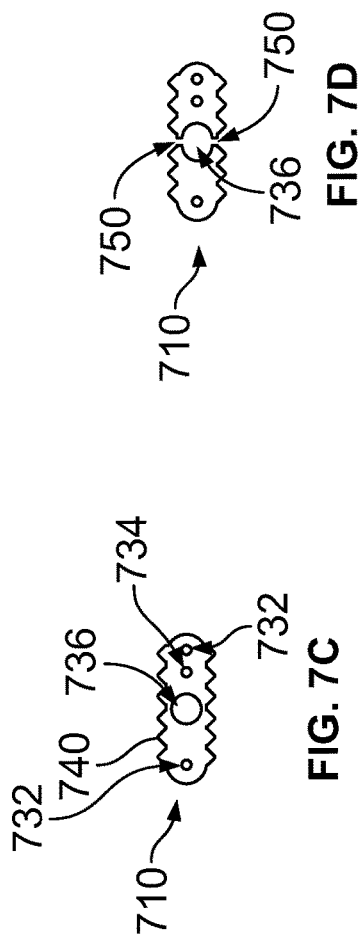

METHOD AND IMPLANTABLE MEDICAL DEVICE FOR REDUCING DEFIBRILLATION IMPEDANCE

BACKGROUND

Embodiments of the present disclosure generally relate to methods and implantable medical devices (IMDs) for reducing impedance for defibrillation therapy. The embodiments are specifically directed to IMDs that have subcutaneous leads.

Some IMDs include circuitry that monitors a patient's heart rhythm to detect arrythmias, such as ventricular tachycardia and/or atrial fibrillation. In response to detecting an arrhythmia, the same or a different IMD may deliver a powerful electrical shock to defibrillate the heart. For example, implantable cardioverter defibrillators (ICDs) are IMDs which include a battery-operated generator that generates high voltage shocks and at least one lead extending from the generator to deliver the shocks. Some ICD leads are intra-cardiac and/or transveous, such that the leads are introduced on or in heart tissue or in surrounding blood vessels.

Some ICD systems are subcutaneous and deliver defibrillation therapy without any intra-cardiac or transveous leads. The subcutaneous ICDs (S-ICD) include at least one subcutaneous lead extending from the generator. The subcutaneous lead is implanted below the skin but outside of the cardiac tissue and blood vessels. The subcutaneous lead may be implanted along an exterior of the ribcage, such as proximate to the sternum. S-ICD systems eliminate risks associated with transveous and/or intra-cardiac implanted leads, such as infections and lead failures that may require surgical intervention.

A drawback of known S-ICD systems is the relatively large size of the generator device. The size may be attributable, at least in part, to the power circuitry used to power the defibrillation therapy. For example, to provide shocks to the heart through intervening biologic tissues with sufficient energy to achieve cardioversion (e.g., restoration of normal heart rhythm), the generator may include a significant volume of energy storage onboard, such as multiple capacitors, to power the shocks. For example, the generator may be controlled to convey electrical power on the order of 1200 V or more to the lead for the shocks. The large size of the generator component increases the complexity of the S-ICD implantation, may cause the patient discomfort post-implantable, and/or may induce body dysmorphic feelings in the patient.

A need remains for methods and implantable medical devices that can achieve satisfactory defibrillation performance without intra-cardiac and/or transveous leads and with a smaller generator than known subcutaneous IMDs.

SUMMARY

In accordance with an embodiment, an implantable medical device (IMD) is provided that includes a lead configured to be operably coupled to a pulse generator and subcutaneously implanted within a patient. The lead includes an electrode configured to receive electrical power from the pulse generator and to provide high-voltage shocks for defibrillation therapy. The electrode has an oblong cross-sectional shape with a major dimension that is at least 10 French (F).

Optionally, the oblong cross-sectional shape of the electrode has a minor dimension that is less than the major dimension and oriented perpendicular to the major dimension. An aspect ratio of the major dimension to the minor dimension may be at least 2:1. The minor dimension may be at least 10 F and the major dimension is greater than 10 F. Optionally, the oblong cross-sectional shape of the electrode includes first and second planar sides that are parallel to each other and first and second curved sides. Each of the first and second curved sides may extend from the first planar side to the second planar side. The oblong cross-sectional shape of the electrode may be an oval. The oblong cross-sectional shape of the electrode may be rectangular with rounded corners. Optionally, the electrode includes a plurality of electrically conductive brick segments that are coupled together in a line.

Optionally, the electrode is a first electrode configured to be located in a parasternal area of the patient, and the lead includes a second electrode configured to provide the high-voltage shocks for the defibrillation therapy. The second electrode may be disposed between the first electrode and the pulse generator along a length of the lead. The second electrode may have an oblong cross-sectional shape. The first electrode may have a first orientation extending from a proximal end of the first electrode to a distal end of the first electrode. The second electrode may have a second orientation extending from a proximal end of the second electrode to a distal end of the second electrode. The first orientation may be transverse to the second orientation when implanted in the patient.

The IMD may include the pulse generator. The pulse generator may be configured to supply electrical power at less than 1000 V through the lead to the electrode to provide the high-voltage shocks. The pulse generator may have a volume less than 50 $cm^3$.

In accordance with an embodiment, a method is provided for producing an implantable medical device (IMD). The method includes forming a lead that is configured to be operably coupled to a pulse generator and subcutaneously implanted within a patient. The method includes securing an electrode on the lead. The electrode is configured to receive electrical power from the pulse generator and to provide high-voltage shocks for defibrillation therapy. The electrode has an oblong cross-sectional shape with a major dimension that is at least 10 F.

Optionally, the oblong cross-sectional shape of the electrode has a minor dimension that is less than the major dimension and is perpendicular to the major dimension. An aspect ratio of the major dimension to the minor dimension may be at least 2:1. The electrode may be a first electrode configured to be located in a parasternal area of the patient. The method may include securing a second electrode to the lead at a location between the first electrode and the pulse generator along a length of the lead. Both the first electrode and the second electrode may be configured to provide the high-voltage shocks for the defibrillation therapy. The method may include implanting the lead such that the first electrode has a first orientation extending from a proximal end of the first electrode to a distal end of the first electrode, and the second electrode has a second orientation extending from a proximal end of the second electrode to a distal end of the second electrode. The first orientation may be transverse to the second orientation.

In accordance with an embodiment, an introducer sheath is provided for implanting a subcutaneous lead into a patient. The introducer sheath includes a tubular body and a gripping element. The tubular body extends a length from a proximal end of the tubular body to a distal end of the tubular body. The tubular body defines an internal cavity that extends the length of the tubular body. The internal cavity is sized and shaped to accommodate a rod of a tunneling tool therethrough. The tubular body defines an array of flushing holes at different locations along the length of the tubular body and at different radial locations along a perimeter of the tubular body. The gripping element projects from the tubular body and is configured to be held by an operator.

Optionally, the internal cavity of the tubular body has an oblong cross-sectional shape to accommodate an oblong shape of one or more shocking electrodes of a subcutaneous lead inserted through the internal cavity. The introducer sheath may include a side-port with a hose and a valve. The hose may be connected to the tubular body and fluidly connected to the internal cavity. The hose may extend from the tubular body to a distal end of the hose that is connected to the valve. The valve may be configured to receive an injection of fluid for emission through the flushing holes into a channel of a patient.

BRIEF DESCRIPTION OF THE DRAWINGS

FIG. 7A illustrates a plan view of a lead according to an embodiment.

FIG. 7B is a side view of a distal portion of the lead shown in FIG. 7A.

FIG. 7C illustrates a cross-sectional shape of a brick segment of the lead taken along line 7C-7C in FIG. 7A.

FIG. 7D illustrates a cross-sectional shape of another brick segment of the lead taken along line 7D-7D in FIG. 7A.

DETAILED DESCRIPTION

Figure 1:
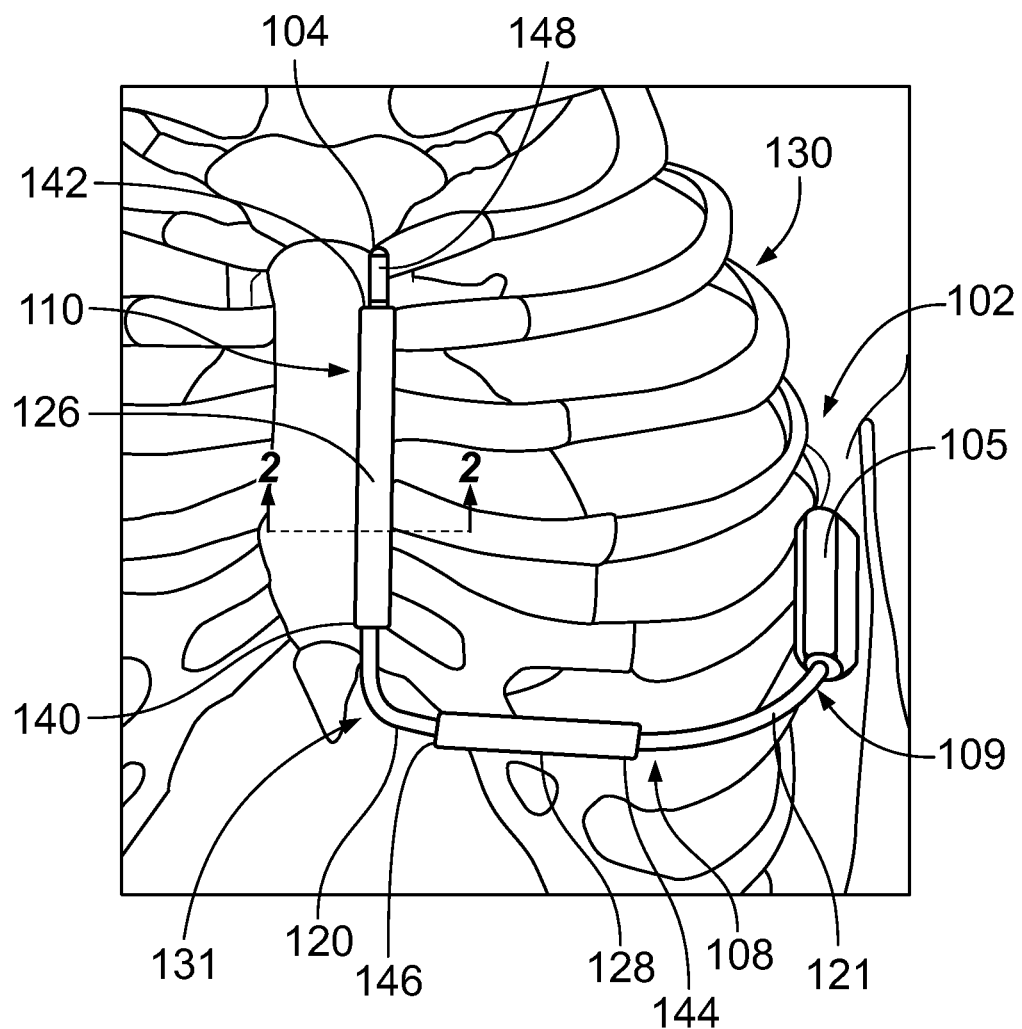
FIG. 1 illustrates a graphical representation of an implantable medical device (IMD) that is configured to apply defibrillation therapy in accordance with embodiments herein.

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Embodiments may be implemented in connection with one or more implantable medical devices (IMDs). Non-limiting examples of IMDs include one or more of neurostimulator devices, implantable leadless monitoring and/or therapy devices, and/or alternative implantable medical devices. For example, the IMD may represent a cardiac monitoring device, pacemaker, cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference.

Additionally or alternatively, the IMD may be a subcutaneous IMD (e.g., a S-ICD) that includes one or more structural and/or functional aspects of the device(s) described in U.S. application Ser. No. 15/973,195, titled "Subcutaneous Implantation Medical Device With Multiple Parasternal-Anterior Electrodes" and filed May 7, 2018; U.S. application Ser. No. 15/973,219, titled "Implantable Medical Systems And Methods Including Pulse Generators And Leads" filed May 7, 2018; U.S. application Ser. No. 15/973,249, titled "Single Site Implantation Methods For Medical Devices Having Multiple Leads", filed May 7, 2018, which are hereby incorporated by reference in their entireties. Further, one or more combinations of IMDs may be utilized from the above incorporated patents and applications in accordance with embodiments herein.

All references, including publications, patent applications and patents, cited herein are hereby incorporated by reference to the same extent as if each reference were individually and specifically indicated to be incorporated by reference and were set forth in its entirety herein.

Terms

The terms "cardiac activity signal", "cardiac activity signals", "CA signal" and "CA signals" (collectively "CA signals") are used interchangeably throughout to refer to measured signals indicative of cardiac activity by a region or chamber of interest. For example, the CA signals may be indicative of impedance, electrical or mechanical activity by one or more chambers (e.g., left or right ventricle, left or right atrium) of the heart and/or by a local region within the heart (e.g., impedance, electrical or mechanical activity at the AV node, along the septal wall, within the left or right bundle branch, within the purkinje fibers). The cardiac activity may be normal/healthy or abnormal/arrhythmic. An example of CA signals includes EGM signals. Electrical based CA signals refer to an analog or digital electrical signal recorded by two or more electrodes, where the electrical signals are indicative of cardiac activity. Heart sound (HS) based CA signals refer to signals output by a heart sound sensor such as an accelerometer, where the HS based CA signals are indicative of one or more of the S1, S2, S3 and/or S4 heart sounds. Impedance based CA signals refer to impedance measurements recorded along an impedance vector between two or more electrodes, where the impedance measurements are indicative of cardiac activity.

The terms "high-voltage shock" and "HV shock" refer to defibrillation stimulus delivered at an energy level sufficient to terminate a defibrillation episode in a heart, wherein the energy level is defined in Joules to be 40 J or more and/or the energy level is defined in terms of voltage to be 750V or more.

The term "defibrillation threshold" and acronym "DFT" refer to a minimum amount of energy needed to be delivered in a high-voltage shock of defibrillation therapy in order to return a heart to a normal rhythm from a condition in which the heart is experiencing a fibrillation dysrhythmia episode.

The term "oblong" as used herein refers to elongated shapes that are longer in at least one dimension than another dimension, such that the oblong shapes are not circular/cylindrical or square/cubic.

The terms "processor," "a processor", "one or more processors" and "the processor" shall mean one or more processors. The one or more processors may be implemented by one, or by a combination of more than one implantable medical device, a wearable device, a local device, a remote device, a server computing device, a network of server computing devices and the like. The one or more processors may be implemented at a common location or at distributed locations. The one or more processors may implement the various operations described herein in a serial or parallel manner, in a shared-resource configuration and the like.

The term "subcutaneous" shall mean below the skin, but not intravenous. For example, a subcutaneous electrode/lead does not include an electrode/lead located in a chamber of the heart, in a vein on the heart, or in the lateral or posterior branches of the coronary sinus.

FIG. 1 illustrates a graphical representation of an implantable medical device (IMD) 102 that is configured to apply defibrillation therapy in accordance with embodiments herein. The IMD 102 in the illustrated embodiment is a subcutaneous implantable medical device (SIMD) that is configured to be implanted in a subcutaneous area exterior to the heart. The SIMD 102 includes a pulse generator 105 and at least one lead 120 that is operably coupled to the pulse generator 105. The "at least one lead" is hereinafter referred to as "the lead." Nevertheless, it should be understood that the term, "the lead," may mean only a single lead or may mean more than one single lead. The lead 120 includes a lead body 121 that is mechanically connected to the pulse generator 105 and extends from the pulse generator 105 to a distal tip 104 of the lead 120.

The pulse generator 105 includes a housing that contains power circuitry and energy storage devices for generating high-voltage shocks (HV shocks) for defibrillation therapy. The housing may be electrically conductive to form or constitute an electrode utilized to deliver the HV shocks. The electrode associated with the housing of the pulse generator 105 is referred to as the "CAN" electrode. The pulse generator 105 may be subcutaneously implanted within a pocket at a mix-axillary position along a portion of the ribcage 130 of the patient.

The lead 120 may be subcutaneously implanted. In particular embodiments, the SIMD 102 is an entirely or fully subcutaneous SIMD. The SIMD may not include a transveous lead. The lead 120 in the illustrated embodiment includes a first or proximal segment 108 that extends from the pulse generator 105 along an inter-costal area between ribs. The lead 120 has a proximal end 109 that mechanically couples to the pulse generator 105, and electrically connects to the pulse generator 105 to establish conductive path(s) to the electrodes of the lead 120. The proximal segment 108 may be laterally oriented to extend along an anterior axillary area of the ribcage 130. The lead 120 has a second or distal segment 110 that extends from the proximal segment 108 to the distal tip 104. The distal segment 110 may extend along the sternum (e.g., over the sternum or parasternally within one to three centimeters from the sternum). The intersection between the distal and proximal segments 108, 110 may be located proximate to the xiphoid process of the patient.

The lead 120 includes at least one electrode that is electrically connected to the pulse generator 105 and delivers the HV shocks for defibrillation therapy. In the illustrated embodiment, the lead 120 has a first or primary electrode 126 disposed along the distal segment 110 and a second or secondary electrode 128 disposed along the proximal segment 108. The electrodes 126, 128 may be referred to as shocking electrodes. The electrodes 126, 128 may be elongated coil electrodes. The lengths of the coil electrodes 126, 128 may be in a range from about 3 cm to about 10 cm. In the illustrated embodiment, the primary electrode 126 is longer than the secondary electrode 128. For example, the primary electrode 126 may be about 8 cm, and the secondary electrode 128 may be above 5 cm. In an embodiment, when the pulse generator 105 generates a HV shock, the pulse generator 105 supplies electrical power to both of the electrodes 126, 128. Both electrodes 126, 128 may deliver the HV shocks based on the received electrical power. The electrodes 126, 128 may concurrently deliver the HV shocks to different areas relative to the heart.

The electrode 126, 128 are spaced apart from each other along the length of the lead 120 by a gap segment 131 of the lead body 121. The gap segment 131 may be proximate to the xiphoid process. The primary electrode 126 may be positioned along an anterior region of the chest, and the secondary electrode 128 may laterally extend between the primary electrode 126 and the pulse generator 105. The electrodes 126, 128 may be subcutaneously positioned at a level that aligns with the heart of the patient for providing a sufficient amount of energy for defibrillation.

The primary electrode 126 may be oriented transverse to an orientation of the secondary electrode 128 when in the implanted position as shown in FIG. 1. For example, the primary electrode 126 has a first orientation extending from a proximal end 140 of the electrode 126 to a distal end 142 of the electrode 126 (defined along the length of the lead 120 relative to the pulse generator 105). The first orientation may be generally parallel to the midsternal line of the patient. The secondary electrode 128 has a second orientation extending from a proximal end 144 of the electrode 128 to a distal end 146 of the electrode 128. The second orientation may be transverse to the first orientation. Optionally, the orientation of the secondary electrode 128 may define an angle between about 60 degrees and 120 degrees (e.g., such as 70 degrees to 110 degrees) relative to the orientation of the primary electrode 126. Due to the orientation, the lead 120 may be referred to as an L-shaped lead. The primary electrode 126 may be referred to as a parasternal electrode. The secondary electrode 128 may be referred to as a transverse electrode.

In an alternative embodiment, the SIMD 102 may lack the secondary electrode 128. For example, the proximal segment 108 may not have any shocking electrodes. The primary electrode 126 may be the only shocking electrode on the lead 120 that delivers the HV shocks supplied from the pulse generator 105.

Optionally, the lead 120 may include one or more sensing electrodes 148 for detection of far field electrogram signals. The sensing electrode(s) 148 may collect subcutaneous cardiac activity (CA) signals in connection with multiple cardiac beats. In the illustrated embodiment, one sensing electrode 148 is disposed at the distal tip 104 of the lead 120. The SIMD 102 may process the CA signals to detect arrhythmias, such as ventricular tachycardia and/or atrial fibrillation. If an arrhythmia is detected, the SIMD 102 may automatically take one or more actions depending on characteristics of the arrhythmia, such as type and severity. The actions may include delivering one or more electrical HV shocks (e.g., shock pulses) via the shocking electrodes 126, 128 in an attempt to achieve cardioversion. Optionally, another IMD may be implanted within the heart, such as a leadless pacemaker. The SIMD 102 may be configured to communicate with the other intra-cardiac IMD. For example, the intra-cardiac IMD may signal to the SIMD 102 when an arrhythmia is detected for the SIMD 102 to deliver the HV shocks in response to receiving the signal.

The SIMD 102 according to the embodiments described herein can achieve satisfactory defibrillation performance without intra-cardiac and/or transveous leads and with a smaller generator than known subcutaneous IMDs. For example, the SIMD 102 may achieve enhanced shocking energy efficiency by lowering the impedance of the shocking electrodes 126, 128 that deliver the HV shocks into the patient tissue. For example, according to Ohm's law (I=V/R), reducing the impedance (R) enables the SIMD 102 to achieve a designated current (I) output at a reduced voltage (V) level from the pulse generator 105. The designated current output may be associated with the defibrillation threshold (DFT) of the patient. The DFT refers to the shock energy necessary to achieve cardioversion (e.g., to return a heart to a normal rhythm from a condition in which the heart is experiencing a fibrillation dysrhythmia episode). Reducing the impedance enables the SIMD 102 to deliver HV shocks at or above the DFT at a lower input voltage level, so the cardioversion is more efficient. Even if the current voltage level provides output current at or above the DFT, reducing the impedance while maintaining a constant voltage may still be beneficial because the output current increases, which enlarges the safety margin to ensure defibrillation is achieved by the shock pulses.

A significant benefit of reducing the impedance is the option to reduce the size and/or power of the pulse generator 105. For example, due to lower impedance the SIMD 102 may be able to provide the same defibrillation therapy at substantially less voltage provided by the pulse generator 105. The pulse generator 105 according to one or more embodiments may have a smaller volume than known SIMDs that provide HV shocks. In an embodiment, the volume of the pulse generator 105 (e.g., the housing) may be less than 50 cm$^3$. For example, the volume of the pulse generator 105 may be less than 40 cm$^3$, such as 35 cm$^3$. The pulse generator 105 may have fewer and/or smaller energy storage devices (e.g., capacitors, battery cells, etc.) than the known SIMDs and/or may have fewer and/or smaller power electronics. In an embodiment, the pulse generator 105 supplies electrical power for the HV shocks at a voltage of less than 1000 V. For example, the SIMD 102 may be able to achieve a clinically acceptable safety margin at voltages less than 900 V, such as less than 850 V. The mass of the pulse generator 105 may be less than 100 grams, such as less than 80 grams.

The relatively small size and weight of the pulse generator 105 may alleviate some patient discomfort experienced with known SIMDs. Furthermore, the pulse generator 105 may be less noticeable to the patient when implanted, which may help avoid body dysmorphia issues. Furthermore, even if the size and/or power capability of the pulse generator 105 is kept similar to the known SIMDs, the increased efficiency may increase the operational lifetime of the SIMD 102 and/or reduce the charge frequency relative to known SIMDs.

The reduction in the impedance may be achieved, at least in part, by the lead 120. For example, at least one of the shocking electrodes 126, 128 may be formed with a modified size and/or shape to reduce the impedance. Clinical trials have experimentally demonstrated that the impedance can be reduced by one or more of (i) increasing the size of the shocking coil(s) along one or more dimensions; (ii) forming the cross-sectional shape of the shocking coil(s) as oblong; and/or (iii) using multiple shocking coils to deliver the HV shocks, such as the two electrodes 126, 128 shown in FIG. 1.

The subcutaneous lead 120, when implanted, may be surrounded at least in part by fat tissue (e.g., lipids) of the patient. The fat may be within adipose tissue, which is adjacent to a fascia layer. Clinical trials have experimentally demonstrated that fat surrounding the electrode(s) increases the impedance relative to the electrode(s) only being surrounded by non-fat tissue in the fascia and/or muscle layers. It has also been observed that fat around the electrode(s) makes the impedance particularly sensitive to electrode cross-sectional size. For example, at tested electrode diameters from 7 F to 11 F implanted within a thin layer of fat, the observed relation was a reduction in impedance of between 6 and 9 ohms for each additional French unit of diameter. As such, larger diameter electrodes experienced lower shocking impedance in the fat than smaller diameter electrodes. With respect to an L-shaped, dual electrode lead 120 as shown in FIG. 1, the inventors have experimentally observed a reduction of 8 ohms per each additional French. The effects of the surrounding tissue on impedance is typically ignored in known systems that use transveous leads because blood and cardiac tissue have little effect on shocking impedance.

In an embodiment, at least one of the shocking electrodes 126, 128 of the lead 120 has an increased size. That shocking electrode 126, 128 may have an oblong cross-sectional area with a major dimension that is at least 10 F (3.33 mm). The major dimension represents the largest or broadest dimension of the cross-sectional area. For example, if the electrode is cylindrical, the major dimension is equivalent to the diameter. The cross-sectional area may include both the major dimension and a minor dimension that is perpendicular (i.e., orthogonal) to the major dimension. The minor dimension is smaller/narrower than the major dimension. The minor dimension represents the smallest or narrowest dimension of the cross-sectional area, which is perpendicular to the major dimension. The size of the shocking coil is formed with a major dimension of at least 10 F in order to achieve a low shocking impedance and maintain a low DFT, even in the presence of fat.

Figure 2A:
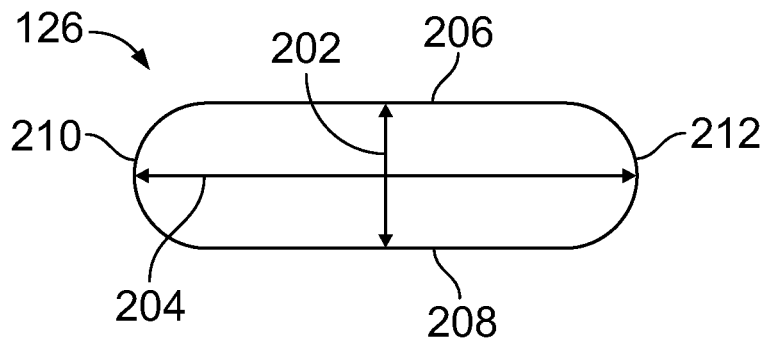
FIG. 2A illustrates a cross-sectional shape of the primary electrode according to a first embodiment.
Figure 2B:
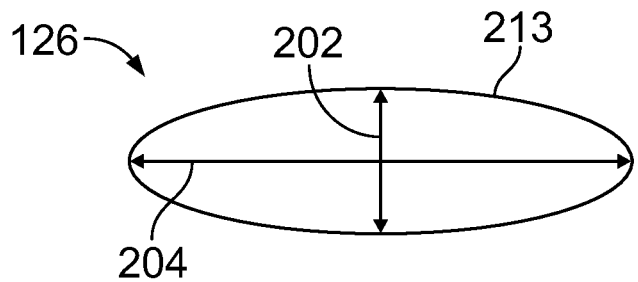
FIG. 2B illustrates the cross-sectional shape of the primary electrode according to a second embodiment.
Figure 2C:
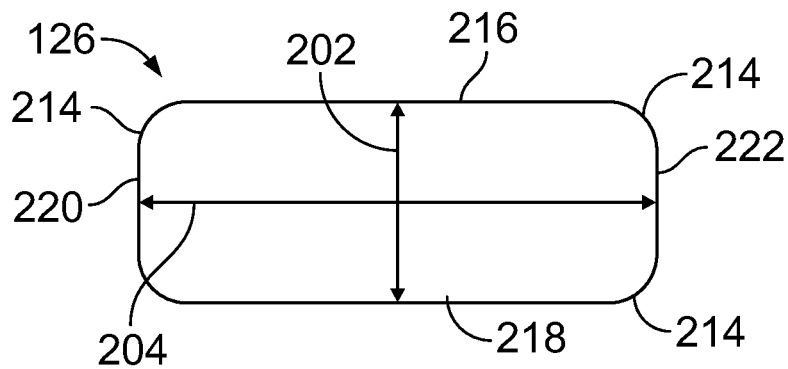
FIG. 2C illustrates the cross-sectional shape of the primary electrode according to a third embodiment.
Figure 2D:
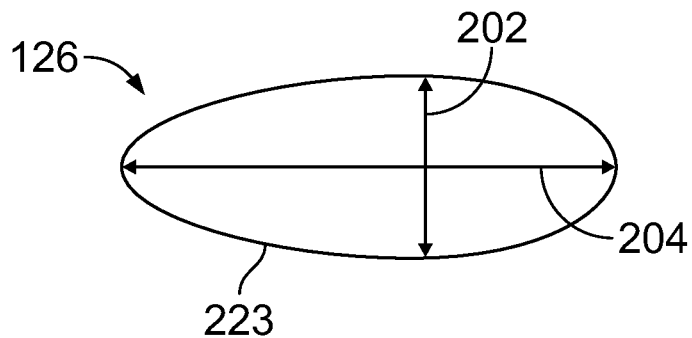
FIG. 2D illustrates the cross-sectional shape of the primary electrode according to a fourth embodiment.

The oblong cross-sectional shape may reduce the shocking impedance. FIG. 2A illustrates a cross-sectional shape of the primary electrode 126 according to a first embodiment. FIG. 2B illustrates the cross-sectional shape of the primary electrode 126 according to a second embodiment. FIG. 2C illustrates the cross-sectional shape of the primary electrode 126 according to a third embodiment. FIG. 2D illustrates the cross-sectional shape of the primary electrode 126 according to a fourth embodiment. The cross-sections in FIGS. 2A-D may be taken through the primary electrode 126 along line 2-2 in FIG. 1. For example, the cross-sectional shapes described herein are cross-sections taken along a plane that is orthogonal to a tangential length direction of the lead 120 at the location of the cross-section. The illustrations in FIGS. 2A-D depict the perimeter shape (e.g., form) of the electrode 126 without showing the conductive elements of the lead 120 and/or electrode 126 within the area defined by the perimeter shapes. Each of the oblong cross-sectional shapes in FIGS. 2A-D has a respective minor dimension 202 and a respective major dimension 204. The minor dimension 202 may represent a thickness of the electrode 126, and the major dimension 204 represents a width of the electrode 126. The major dimension 204 is greater than the minor dimension 202. In an embodiment, the major dimension 204 is at least 10 F (3.33 mm).

The primary electrode 126 in FIG. 2A has a shape referred to herein as a racetrack. The electrode 126 has a first planar side 206 and a second planar side 208. The thickness of the electrode (e.g., the minor dimension 202) is defined between the first and second planar sides 206, 208. The planar sides 206, 208 may be parallel to each other. The electrode 126 has a first curved side 210 and a second curved side 212. Each of the curved sides 210, 212 extends from the first planar side 206 to the second planar side 208. The width of the electrode (e.g., the major dimension 204) is defined between the first and second curved sides 210, 212. In an embodiment, the curved sides 210, 212 have a radius of curvature that is half of the thickness of the electrode 126 (e.g., the diameter of the curvature is equal to the electrode thickness). The curved sides 210, 212 may have a different radius in other embodiments.

The primary electrode 126 in FIG. 2B has an oval cross-sectional shape in the form of an ellipse. For example, the perimeter of the elliptical electrode 126 has only curved sides 213; no planar surfaces. The perimeter may be traced by a point moving in a plane so that the sum of its distances from two focal points is constant.

The primary electrode 126 in FIG. 2C has a rectangular cross-sectional shape with rounded corners 214. For example, the electrode has two broad sides 216, 218 spaced apart from each other to define the thickness (e.g., minor dimension 202), and two narrow sides 220, 222 spaced apart from each other to define the width (e.g., major dimension 204). The broad sides 216, 218, and the narrow sides 220, 222 may be planar. The corners 214 are located at the intersections between the sides 216, 218, 220, 222. The corners 214 are curved to avoid snagging on patient tissue and/or implant tools.

The primary electrode 126 in FIG. 2D has an over cross-sectional shape that is not an ellipse. For example, unlike the ellipse in FIG. 2B that has symmetry along both the minor dimension 202 and the major dimension 204, the oval electrode 126 in FIG. 2D has symmetry only along the major dimension 204. The oval electrode 126 has only curved sides 223 like the ellipse in FIG. 2B.

Although four oblong shapes are shown in FIGS. 2A-2D, the shocking electrodes may have a different oblong cross-sectional shape in other embodiments. For example, the electrode 126 may have a trapezoidal cross-sectional shape with rounded corners. Relative to the rectangular shape in FIG. 2C, the trapezoidal shape may be achieved by forming the first broad side 216 to be shorter than the opposite, second broad side 218, such that the narrow sides 220, 222 angle towards each other and are not parallel.

The following description may refer to any of the electrodes 126 shown in FIGS. 2A-D. The major dimension 204 is greater than the minor dimension 202. The minor dimension 202 (e.g., the thickness) may be at least 3 F (1 mm). When the thickness is less than 3 F, the impedance may be undesirably high, as observed through experimentation. The cross-sectional area of the electrode 126 may be at least 64 $F^2$ (e.g., at least 7.1 mm$^2$). In an embodiment, the minor dimension is at least 10 F, so the major dimension 204 is greater than 10 F (e.g., 11 F, 13 F, 15 F, 20 F, 30 F, etc.). For example, the cross-sectional area of the electrode 126 may be at least 80 $F^2$ (e.g., at least 9 mm$^2$).

In an embodiment, the cross-sectional shape of the shocking electrode 126 has an aspect ratio of the major dimension 204 to the minor dimension 202 that is at least 2:1. For example, the shape of the oblong electrode 126 may be at least twice as wide as the electrode 126 is thick. The minor dimension 202 of the electrode 126 cross-sectional shape may be 8 F, and the major dimension 204 is at least 16 F. In another example, the minor dimension 202 may be 10 F, and the major dimension 204 is at least 20 F. The inventors have experimentally determined that a 10 F by 20 F elliptical coil electrode 126, as shown in FIG. 2B, may reduce shocking impedance by about 20% relative to a cylindrical coil electrode with a 10 F diameter.

The wide aspect ratio of at least 2:1 may enable the electrode 126 to lay flat when implanted in a channel of the patient. The flat shape may reduce the likelihood of the lead 120 twisting within the channel and/or deviating from an installed position. The flat shape may also reduce patient discomfort, as the electrode 126 may be thinner than known cylindrical electrodes. In one or more embodiments, the thickness of the electrode 126 may be in a range from 6 F to about 15 F (2 mm to about 5 mm), to retain a relatively thin form. In an example, the electrode 126 has a thickness of 12 F (4 mm) and a width of 24 F (8 mm). Optionally, the aspect ratio may be greater than 2:1, such as 3:1 or 4:1. In one or more embodiments, the width of the electrode 126 may be in a range from 20 F to about 50 F (6.66 mm to about 16.66 mm).

In an embodiment, the dual-electrode L-shaped lead 120 shown in FIG. 1 can be implanted via a single incision site near the xiphoid process. The proximal segment 108 may be loaded along a first channel that laterally extends from the incision site to the subcutaneous pocket that contains the pulse generator 105 for connecting to the pulse generator 105. The distal segment 110 may be loaded along a parasternal channel that extends from the incision site. Optionally, sutures may be applied to secure the lead 120 to the surrounding tissue and retain the lead 120 in the implanted position.

In an experimental example, it was determined that a subcutaneous lead according to known SIMDs with a single parasternal coil electrode having a cylindrical shape with a 9 F diameter experienced a shocking impedance of about 60 ohms. Modifying the shape and size of the single parasternal coil electrode to have the racetrack shape as shown in FIG. 2A with a thickness of 10 F and a width of 30 F resulted in an impedance reduction. Furthermore, coupling a second coil electrode with that racetrack-shaped coil electrode to provide the L-shaped dual-electrode lead 120 of FIG. 1 resulted in an additional impedance reduction to about 40 ohms (which is 33% less than the 60 ohms achieved using the cylindrical electrode).

In an embodiment, the SIMD 102 includes the dual-electrode lead 120 (as shown in FIG. 1), and the secondary shocking electrode 128 (e.g., transverse electrode) also has an oblong cross-sectional shape. The cross-sectional shape of the secondary electrode 128 may have a major dimension that is at least 10 F (3.33 mm). The cross-sectional shape of the secondary electrode 128 may be any of the shapes shown in FIGS. 2A-2D. The two electrodes 126, 128 may have the same cross-sectional shape and sizes. For example, both electrodes 126, 128 may have the same racetrack shape as shown in FIG. 2A with the same dimensions.

In an embodiment, portions of the lead body 121 outside of the electrodes 126, 128 may have cylindrical cross-sectional shapes. The cylindrical shapes may assist with bending and twisting the lead 120 during implant, such as to achieve the desired L-shaped bend at the gap section 131 between the electrodes 126, 128. The cylindrical lead body 121 may have a smaller diameter than the major dimensions of the electrodes 126, 128. Optionally, the cross-sectional shape of the lead body 121 may be oblong and consistent with the shape of the electrodes 126, 128, such that the lead 120 is approximately uniform along the length.

In a first alternative embodiment, the secondary electrode 128 may have a different oblong shape than the primary electrode 126. For example, the secondary electrode 128 may have the rectangular shape in FIG. 2C, and the primary electrode 126 may have the racetrack shape, an oval (e.g., elliptical) shape, a trapezoidal shape, or the like. In a second alternative embodiment, the primary and secondary electrodes 126, 128 may have different dimensions. For example, the primary electrode 126 may be wider than the secondary electrode 128, even if the two electrodes have the same oblong cross-sectional shape. In an example application, the primary electrode 126 may be 3 mm (9 F) thick and 10 mm (30 F) wide, and the secondary electrode 128 may be 3 mm (9 F) thick and 5 mm (15 F) wide. In a third alternative embodiment, the secondary electrode 128 may not have an oblong cross-sectional shape. For example, the secondary electrode 128 may have a cylindrical shape. In a fourth alternative embodiment, the secondary electrode 128 may have the oblong cross-sectional shape, while the primary electrode 126 is cylindrical.

Optionally, one or both of the electrodes 126, 128 that are oblong may include an energy directivity layer along one of the broad surfaces for directing the HV shocks inward towards the thoracic cavity and the heart. For example, the oblong shapes shown in FIGS. 2A-D enable defining one of the broad sides as a heart-facing side and the opposite broad side as a back side. A conductive shield layer and/or an insulator layer may be applied on the back side of the electrodes 126, 128 prior to implant. When implanted, the shield layer and/or insulator layer may serve to focus the shocking energy in a direction towards the thoracic cavity and limit the shocking energy that dissipates in directions away from the thoracic cavity.

During implantation, air that is present within the channel of the patient may surround at least a portion of the shocking electrode(s) 126, 128. The air may increase the shocking impedance by providing insulation between the electrode(s) 126, 128 and the body fluids/tissues. Flushing the body channel(s) with saline or another fluid may exclude trapped air from the channel(s) and provide a more favorable interface for the electrode(s) 126, 128 with reduced shocking impedance. During clinical investigations, it was observed that flushing saline around the shocking electrode(s) can reduce shocking impedance in the range of about 9% to 13% relative to not flushing. Known methods of flushing fluid into dead-end body channels may be messy, may require multiple injections, and/or may not adequately wet the entire length of the shocking electrodes.

Figure 3:
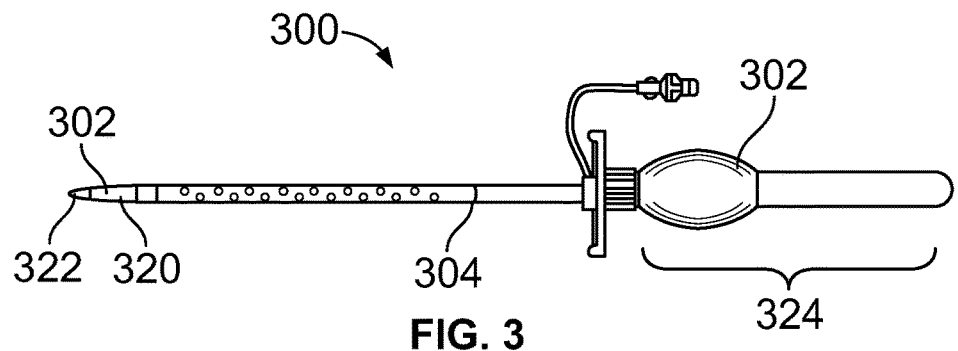
FIG. 3 illustrates an implant tool assembly for implanting a subcutaneous lead according to an embodiment.

FIG. 3 illustrates an implant tool assembly 300 for implanting a subcutaneous lead according to an embodiment. The implant tool assembly 300 may be used to tunnel a subcutaneous channel through a patient, and to introduce a subcutaneous lead into the channel. The subcutaneous lead may be the lead 120 shown in FIG. 1. For example, the implant tool assembly 300 may be used to implant subcutaneous leads that have at least one shocking electrode that has an oblong cross-sectional shape with a major dimension of at least 10 F. The implant tool assembly 300 includes a tunneling tool 302 and an introducer sheath 304. The introducer sheath 304 enables convenient and effective fluid injection for flushing a channel formed by the tunneling tool 302. The fluid that is injected may be a saline solution. The fluid injection may occur prior to introducing the subcutaneous lead 120 into the channel. Alternatively, the lead 120 may be within the sheath 304 and the channel during the fluid injection, such that the flushing occurs with the lead 120 implanted. The sheath 304 is designed to create a fluid (e.g., saline) interface that surrounds the lead 120 and exclude air bubbles from the channel, which reduces the shocking impedance. The implant tool assembly 300 can be used for single incision implants or multi-incision implants.

Figure 4:
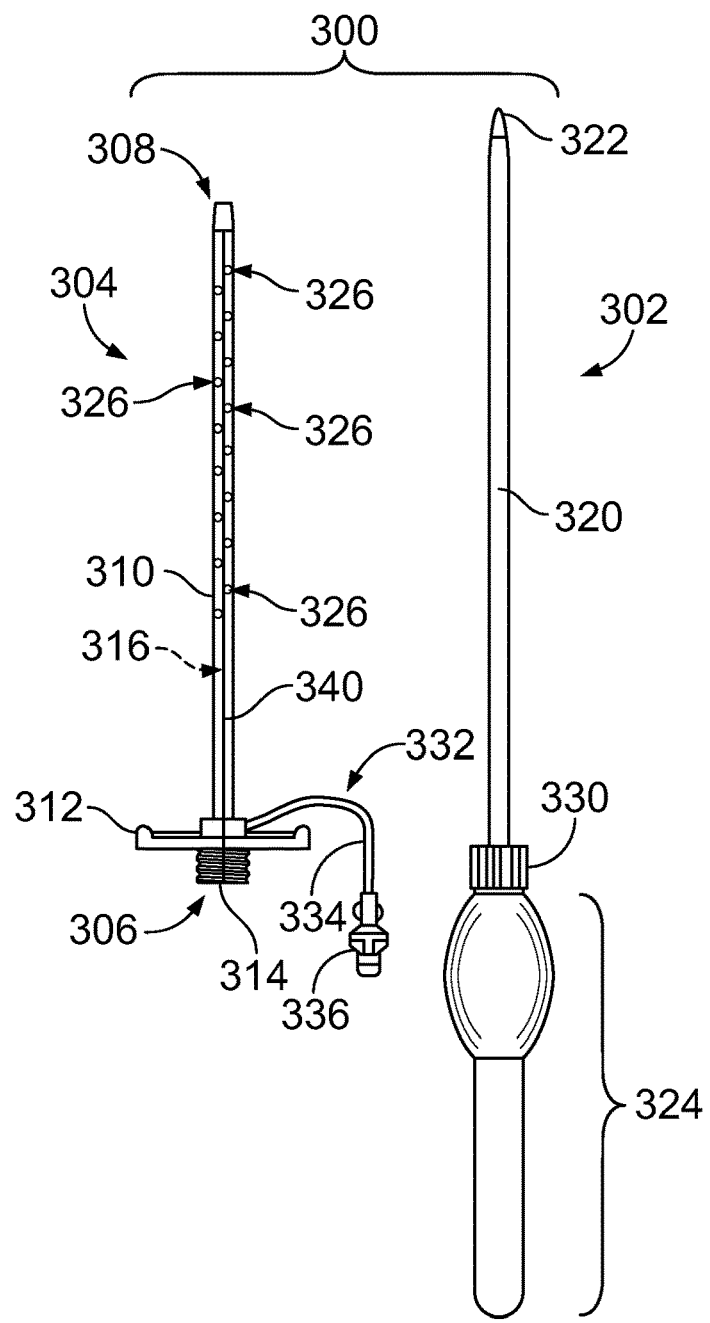
FIG. 4 illustrates the implant tool assembly of FIG. 3 in a disassembled state.

FIG. 4 illustrates the implant tool assembly 300 in a disassembled state. The introducer sheath 304 is elongated and extends from a proximal end 306 to a distal end 308. The sheath 304 includes a tubular body 310 that is hollow. The sheath 304 includes a gripping element 312 projecting from the tubular body 310. The gripping element 312 may be located at or near the proximal end 306. The gripping element 312 may be a flange, one or more tabs, a ring-shaped handle, or the like. The gripping element 312 provides a feature for the operator (e.g., doctor or technician) to hold onto when manipulating the sheath 304. The sheath 304 defines an internal cavity 316 that extends the length of the sheath 304 from the proximal end 306 to the distal end 308. The sheath 304 defines openings to the internal cavity 316 at both ends 306, 308. The internal cavity 316 is sized and shaped to permit a rod 320 of the tunneling tool 302 to extend through the internal cavity 316. As shown in FIG. 3, when the implant tool is assembled and the rod 320 is within the internal cavity 316, a distal tip 322 of the rod 320 may project beyond the distal end 308 of the sheath 304. A handle segment 324 of the tunneling tool 302 may be adjacent to the proximal end 306 of the sheath 304.

During implantation, the sheath 304 may receive the lead 120 after the tunneling tool 302 is extracted from the sheath 304. The internal cavity 316 is sized and shaped to accommodate the oblong cross-sectional shapes of the shocking electrodes 126, 128 of the lead 120. Optionally, the tubular body 310 may have an oblong cross-sectional shape that matches the cross-sectional shape of one or both shocking electrodes 126, 128. Alternatively, the tubular body 310 may be cylindrical and sized such that the internal diameter of the internal cavity 316 is larger than the major dimension 204 of the electrodes 126, 128.

The introducer sheath 304 includes flushing holes 326 that extend through a wall of the tubular body 310 to fluidly connect the internal cavity 316 to an external environment outside of the sheath 304. The flushing holes 326 may be disposed at different locations along the length of the tubular body 310 between the gripping element 312 and the distal end 306. In the illustrated embodiment, the flushing holes 326, on average, may be located closer to the distal end 306 than to the gripping element 312. The flushing holes 326 may be disposed at different radial locations along the perimeter (e.g., circumference) of the tubular body 310. For example, the flushing holes 326 may be arranged in an array that extends radially and longitudinally along the tubular body 310. The flushing holes 326 may emit the fluid (e.g., saline solution) that is injected into the internal cavity 316 such that the fluid is ejected from the sheath 304 at a different locations and in different directions. Ejecting the fluid at different locations and directions from the sheath 304 may provide more reliable, effective, and/or cleaner establishment of the fluid-electrode interface without air bubbles, relative to ejecting fluid through only the opening at the distal end 306.

In an embodiment, the sheath 304 includes a side-port 332 that is connected to the tubular body 310 proximate to the proximal end 306. The side-port 332 includes a hose 334 that is fluidly connected to the internal cavity 316. In the illustrated embodiment, the hose 334 is connected to the tubular body 310 at a location proximate to the gripping element 312, such as just distal of the gripping element 312 (e.g., between the gripping element 312 and the array of flushing holes 326). The side-port 332 is designed to receive the fluid used to flush the channel of the patient. A distal end of the side-port 332 may include a valve 336 that is coupled to the hose 334. The flushing fluid may be injected through the valve 336. In an embodiment, the valve 336 may be a stop-cock valve with a lure lock to accommodate a syringe that injects the fluid.

The sheath 304 optionally includes a locking element 314 for selectively securing the sheath 304 to the tunneling tool 302. The locking element 314 in the illustrated embodiment is a threaded segment of the tubular body 310. The tunneling tool 302 includes a complementary rotatable threaded nut 330 for threadably coupling to the locking element 314. Alternatively, the locking element 314 may be a bayonet slot, a latch, or the like. The locking element 314 may be located at or near the proximal end 306. The tunneling tool 302 may be locked to the sheath 304 when the implant tool assembly 302 is in the assembled state shown in FIG. 3 and the implant tool assembly 302 is inserted through an incision of the patient to form a channel in the patient. After the channel is formed, the locking element 314 may be uncoupled from the tunneling tool 302 to permit the tunneling tool 302 to be extracted from the sheath 304 and the channel of the patient, while the sheath 304 remains in place within the channel.

The sheath 304 optionally may be splitable. For example, the sheath 304 may define at least one linear seam 340 along all or at least a majority of the length. Each seam 340 represents an area in which the wall thickness is reduced relative to the wall thickness adjacent to the seam 340. After the lead 120 is implanted through the sheath 304 and the channel is flushed, the sheath 304 may be split or divided to enable extracting the sheath 304 without interfering with the positioning of the lead 120. In an embodiment, an operator (e.g., doctor or technician) may pull two parts of the gripping element 312 in opposite directions away from the seam 340 with sufficient force to cause the sheath 304 to split apart at the seam(s) 340. The sheath 304 may split into two parts which can individually be removed from the channel of the patient without dislodging the lead 120. In another embodiment, the sheath 304 may include a cutting element that slits the seam(s) 340 to provide the splitting effect.

The following description refers to an implant procedure of a subcutaneous IMD (SIMD) utilizing the implant tool assembly 300 according to an embodiment. The order of these steps may be rearranged unless not practically possible based on the context of the steps. First, an operator makes a subcutaneous pocket in a sub-axillary area of the patient for accommodating the pulse generator 105. Then, a 2 cm long incision is made in the region of the xyphoid process. The implant tool assembly 300 in the assembled state shown in FIG. 3 is introduced by blunt dissection while the tip 322 of the rod 320 is directed to create a parasternal channel as close as possible to the surface of the fascia about 1 cm to the right and/or left of the xyphoid process.

Once inserted to the desired depth, the tunneling tool 302 is removed, while the sheath 304 remains within the channel. The next step may be saline flushing. A saline-filled syringe may be attached to the valve 336 of the side-port 332 for injection of saline. The operator may cover the opening at the proximal end 306 of the tubular body 310 with a thumb, cork, or cap. Optionally, the sheath 304 may include a hemostasis valve which blocks the opening at the proximal end 306. The saline that is injected into the sheath 304 may be discharged to fill the small cavity remaining at the distal dead-end of the channel and some of the saline is ejected into the rest of the channel through the flushing holes 326 incorporated into the walls of the sheath 304 to uniformly wet the inside of the parasternal channel.

The distal segment 110 of the lead 120 may be inserted into the sheath 304 after the parasternal channel is flushed. After placement of the distal segment 110, the process described above may be essentially repeated to form a transverse channel connecting the parasternal channel to the pocket that houses the pulse generator 105. For example, a second implant tool assembly 300 may be used to form the transverse channel. The second implant tool assembly 300 may be similar to the first implant tool assembly 300 used to form the parasternal channel and implant the distal segment 110 of the lead 120. The tunneling tool 302 of the second assembly used to form the transverse channel may be only slightly different than the one used to form the parasternal channel, such as longer. Following the transverse placement of the second introducer sheath 304 and the extraction of the tunneling tool 302, the transverse channel may be flushed similar to the flushing of the parasternal channel. The proximal segment 108 of the lead 120 may be inserted into the second introducer sheath 304 and the wetted transverse channel. The proximal end 109 of the lead 120 is then connected to the pulse generator 105.

Both the first and second introducer sheaths 304 are removed after implant of the corresponding segments 110, 108 of the lead 120. For example, the sheaths 304 may be splitable (e.g., peelable, slitable, etc.) to enable extracting the sheaths 304 from around the lead 120 with the lead 120 intact. Optionally, both sheaths 304 may be removed after the entire lead 120 is implanted. Alternatively, the first sheath 304 may be removed prior to implanting part of the lead 120. For example, the first sheath 304 may be removed prior to implanting the proximal segment 108 into the transverse channel using the second sheath 304.

Figure 5:
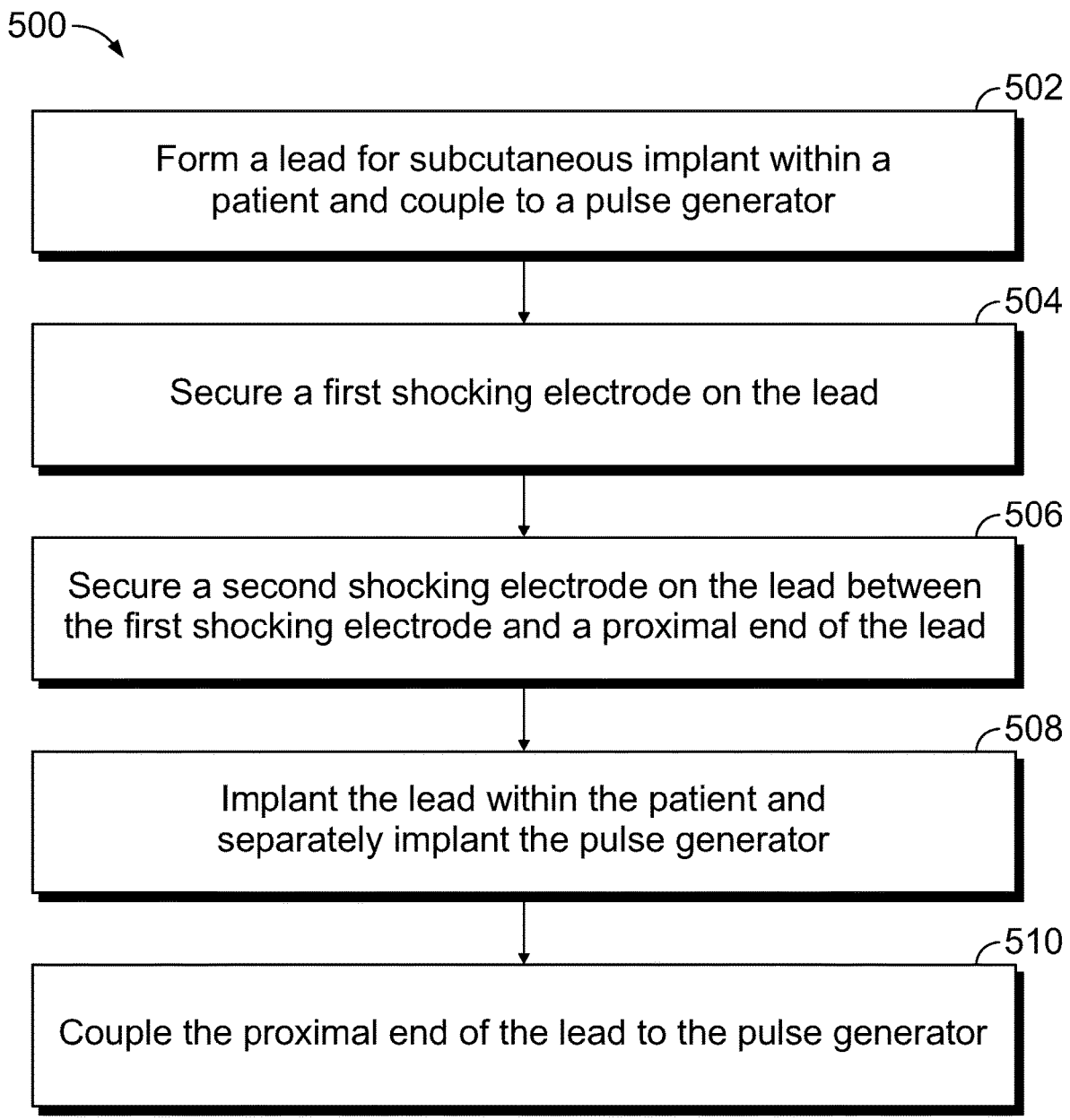
FIG. 5 is a flow chart of a method for producing an implantable medical device (IMD) according to an embodiment.

FIG. 5 is a flow chart 500 of a method for producing an implantable medical device (IMD) according to an embodiment. The method may include additional steps than shown in FIG. 5, fewer steps than shown in FIG. 5, and/or different steps than shown in FIG. 5. The method is described with reference to the SIMD 102 shown in FIG. 1, although the method may be performed with other leads and IMDs. At step 502, a lead 120 is formed that is configured to be operably coupled to a pulse generator 105. The lead 120 is also configured to be subcutaneously implanted with a patient.

At step 504, an electrode 126 (e.g., a shocking electrode) is secured on the lead 120. The electrode 126 is configured to receive electrical power from the pulse generator 105 and to provide high-voltage shocks for defibrillation therapy for the patient. The electrode 126 has an oblong cross-sectional shape with a major dimension 202 that is at least 10 F. The oblong cross-sectional shape of the electrode 126 may have a major dimension 204 that is greater than the minor dimension 202, and an aspect ratio of the major dimension 204 to the minor dimension 202 may be at least 2:1.

In a first example, the oblong cross-sectional shape of the electrode 126 includes first and second planar sides 206, 208 that are parallel to each other and first and second curved sides 210, 212. Each of the first and second curved sides 210, 212 extends from the first planar side 206 to the second planar side 208. The electrode 126 may have other oblong cross-sectional shapes in other embodiments, such as rectangular with rounded corners or oval (e.g., elliptical, egg-shaped, or the like).

At step 506, a second electrode 128 (e.g., shocking electrode) is secured to the lead 120 at a location (along the lead length) between the first electrode 126 and a proximal end 109 of the lead 120 that connects to the pulse generator 105. Both the first electrode 126 and the second electrode 128 may be configured to provide the high-voltage shocks for the defibrillation therapy.

At step 508, the lead 120 is implanted within the patient. The lead 120 may be implanted such that the first electrode 126 has a first orientation and the second electrode 128 has a second orientation, wherein the first orientation is transverse to the second orientation. For example, the first electrode 126 may be located in a parasternal area of the patient, and the second electrode 128 may laterally extend along an inter-costal area between ribs of the patient. Also at step 508, the pulse generator 105 is separately implanted into a subcutaneous pocket within the patient. The pulse generator 105 may be located at a sub-axillary area of the patient.

At step 510, a proximal end 109 of the lead 120 is mechanically coupled to, and electrically connected to, the pulse generator 105 within the patient to establish a conductive path from the pulse generator 105 to the shocking electrodes 126, 128. In an embodiment, the pulse generator may have a volume less than 50 $cm^3$ and/or may supply electrical power at less than 1000 V to the electrodes 126, 128 to provide the high-voltage shocks.

Figure 6:
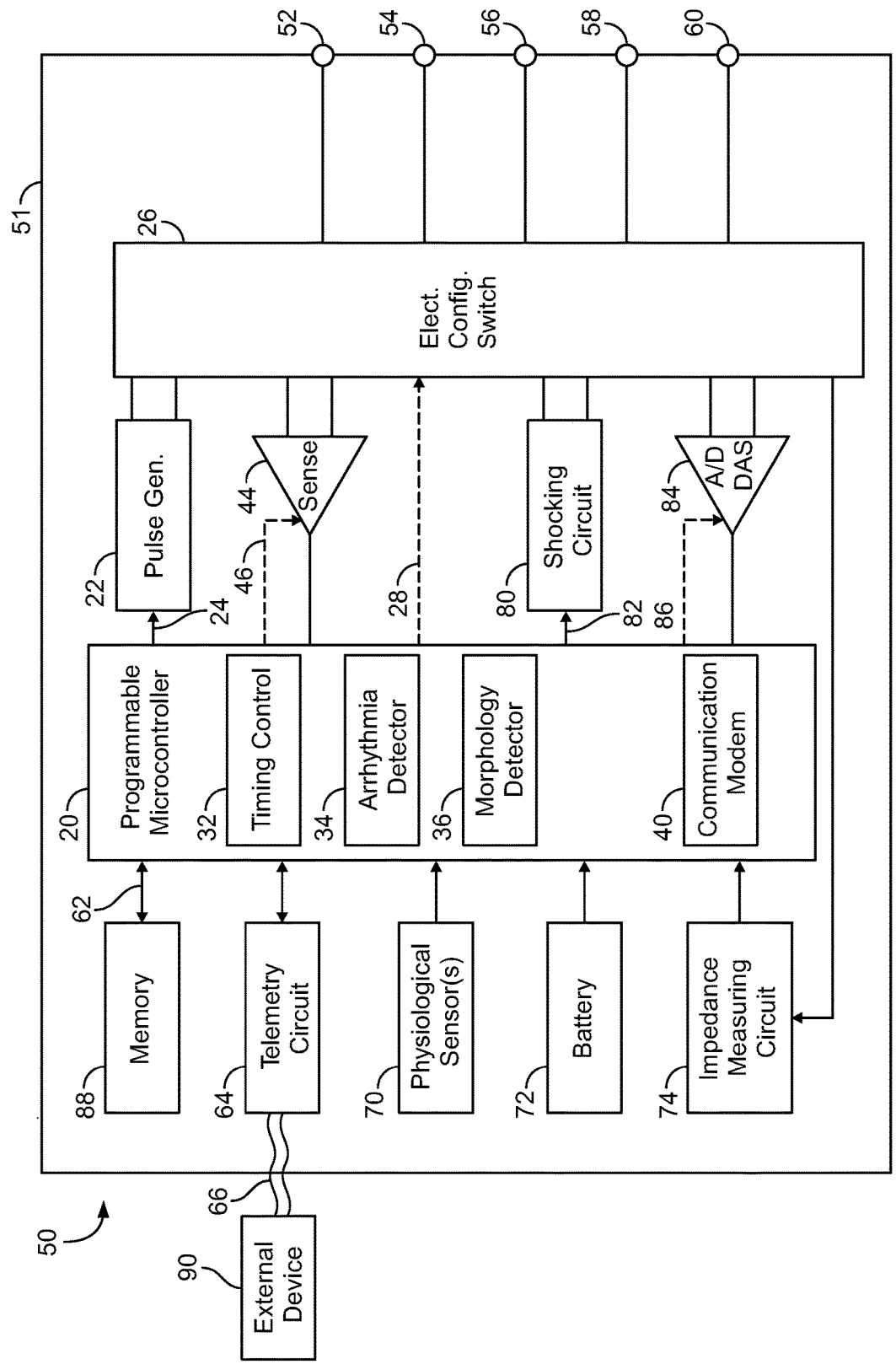
FIG. 6 shows a block diagram of an IMD that is configured to be implanted into a patient.

FIG. 6 shows a block diagram of an IMD 50 that is configured to be implanted into a patient. The IMD 50 may represent the SIMD 102 shown in FIG. 1. The IMD 50 may be implemented to monitor ventricular activity alone, or both ventricular and atrial activity through sensing circuit. The IMD 50 may treat both fast and slow arrhythmias with stimulation therapy, including cardioversion, pacing stimulation, an implantable cardioverter defibrillator, suspend tachycardia detection, tachyarrhythmia therapy, and/or the like.

The IMD 50 has a device case (or housing) 51 to hold the electronic/computing components. The case 51 (which can also be referred to as the "housing," "can," "encasing," or "case electrode") may be programmably selected to function as an electrode for certain sensing modes. Case 51 further includes a connector (not shown) with at least one terminal 52 and optionally additional terminals 54, 56, 58, 60. The terminals may be connected to electrodes that are located in various locations within and about the heart. The type and location of each electrode may vary. For example, the electrodes may include various combinations of ring, tip, coil, shocking electrodes, and the like.

The IMD 50 includes a programmable microcontroller 20 that controls various operations of the IMD 50, including cardiac monitoring and stimulation therapy. Microcontroller 20 includes a microprocessor (or equivalent control circuitry), RAM and/or ROM memory, logic and timing circuitry, state machine circuitry, and I/O circuitry. Microcontroller 20 includes an arrhythmia detector 34 that is configured to cardiac activity data to identify potential AF episodes as well as other arrhythmias (e.g., Tachycardias, Bradycardias, Asystole, etc.).

An electrode configuration switch 26 is optionally provided to allow selection of different electrode configurations under the control of the microcontroller 20. The electrode configuration switch 26 may include multiple switches for connecting the desired electrodes to the appropriate I/O circuits, thereby facilitating electrode programmability. The switch 26 is controlled by a control signal 28 from the microcontroller 20. Optionally, the switch 26 may be omitted and the I/O circuits directly connected to a housing electrode.

The IMD 50 further includes a chamber pulse generator 22 that generates stimulation pulses for connecting the desired electrodes to the appropriate I/O circuits, thereby facilitating electrode programmability. The pulse generator 22 is controlled by the microcontroller 20 via control signals 24. The IMD 50 includes a sensing circuit 44 selectively coupled to one or more electrodes that perform sensing operations through the switch 26 to detect cardiac activity. The sensing circuit 44 may include dedicated sense amplifiers, multiplexed amplifiers, or shared amplifiers. The sensing circuit 44 may operate in a unipolar sensing configuration or a bipolar sensing configuration. The output of the sensing circuit 44 is connected to the microcontroller 20 which, in turn, triggers, or inhibits the pulse generator 22 in response to the absence or presence of cardiac activity. The sensing circuit 44 receives a control signal 46 from the microcontroller 20 for purposes of controlling the gain, threshold, polarization, and timing of any blocking circuitry (not shown) coupled to the sensing circuit.

The IMD 50 further includes an analog-to-digital A/D data acquisition system (DAS) 84 coupled to one or more electrodes via the switch 26 to sample cardiac signals across any pair of desired electrodes. The A/D DAS 84 is controlled by a control signal 86 from the microcontroller 20.

The IMD 50 is communicatively connected to an external device 90. The external device 90 may represent the external device 16 in FIG. 1. The external device 90 may communicate with a telemetry circuit 64 of the IMD 50 through a communication link 66. The external device 90 facilitates access by physicians to patient data as well as permitting the physician to review real-time cardiac signals while collected by the IMD 50.

The microcontroller 20 is coupled to a memory 88 by a suitable data/address bus 62. The memory 88 stores the programmable operating parameters used by the microcontroller 20 and/or data associated with the detection and determination of arrhythmias.

The IMD 50 may further include one or more physiologic sensors 70 adjust pacing stimulation rates, detect changes in cardiac output, changes in the physiological condition of the heart, and/or diurnal changes in activity (e.g., detecting sleep and wake states). Examples of physiological sensors 70 might include sensors that, for example, sense respiration rate, pH of blood, ventricular gradient, activity, body movement, position/posture, minute ventilation (MV), and/or the like.

The battery 72 provides operating power to all of the components in the IMD 50. The battery 72 is capable of operating at low current drains for long periods of time, and is capable of providing a high-current pulses (for capacitor charging) when the patient requires a shock pulse (e.g., in excess of 2 A, at voltages above 2 V, for periods of 10 seconds or more).

The IMD 50 further includes an impedance measuring circuit 74, which can be used for many things, including sensing respiration phase. The IMD 50 is further equipped with a communication modem (modulator/demodulator) 40 to enable wireless communication with the external device 90 and/or other external devices.

The IMD 50 includes a shocking circuit 80 controlled by control signals 86 generated by the microcontroller 20. The shocking circuit 80 generates shocking pulses of low (e.g., up to 0.5 joules), moderate (e.g., 0.5-10 joules), or high energy (e.g., 11 to 40 joules), as controlled by the microcontroller 20.

The microcontroller 20 may include other dedicated circuitry and/or firmware/software components, such as a timing control (module) 32 and a morphology detector (module) 36. The timing control 32 is used to control various timing parameters, such as stimulation pulses (e.g., pacing rate, atria-ventricular (AV) delay, atrial interconduction (A-A) delay, ventricular interconduction (V-V) delay, etc.) as well as to keep track of the timing of RR-intervals, refractory periods, blanking intervals, noise detection windows, evoked response windows, alert intervals, marker channel timing, and the like. The morphology detector 36 is configured to review and analyze one or more features of the morphology of cardiac activity signals, such as the morphology of detected R waves to determine whether to include or exclude one or more beats from further analysis.

FIG. 7A illustrates a plan view of a lead 702 according to an embodiment. The lead 702 may be the lead 120 shown in FIG. 1. The lead 702 includes a primary shocking electrode 704 and a secondary shocking electrode 706. FIG. 7B is a side view of a distal portion 708 of the lead 702 shown in FIG. 7A. In an embodiment, the primary electrode 704 is segmented into plural pieces, referred to herein as brick segments 710. FIG. 7C illustrates a cross-sectional shape of one of the brick segments 710 taken along line 7C-7C in FIG. 7A. FIG. 7D illustrates a cross-sectional shape of another one of the brick segments 710 taken along line 7D-7D in FIG. 7A.

The primary shocking electrode 704 and the secondary shocking electrode 706 optionally may represent the primary shocking electrode 126 and the secondary shocking electrode 128, respectively. For example, the primary electrode 704 may have an oblong cross-sectional shape, as shown in FIGS. 7C and 7D. The secondary electrode 128 may have a cylindrical cross-sectional shape in the illustrated embodiment. In an alternative embodiment, the secondary electrode 128 has an oblong cross sectional shape like the primary electrode 704.

The brick segments 710 may be discrete chips or pieces that are mechanically coupled together in a line to define the primary electrode 704. The brick segments 710 maybe replicas or copies of one another. Each brick segment 710 may have an oblong cross sectional shape. Adjacent brick segments 710 couple together at seams 712. In an embodiment, as shown in FIG. 7B, the brick segments 710 are nested together at the seams 712. For example, at each seam 712, one of the brick segments 710 has a concave mating surface 714 and the other brick segment 710 has a convex mating surface 716 that nests into the concave mating surface 714. Due to the nesting, the curved surfaces 714, 716 are not visible in the plan view of FIG. 7A. The term "brick segment" refers to how the pieces in aggregate form the electrode 704, without denoting or requiring any specific shape. Thus, the brick segments 710 optionally may not have rectangular prism shapes with planar sides.

The brick segments 710 may be secured together via one or more cables 718 that extend across the seams 712. The cable(s) 718 provide mechanical support for retaining the brick segments 710 in the coupled state as well as the general elongated shape of the electrode 704. The cables 718 are shown in more detail in FIG. 8. The tension of the cable(s) 718 may be adjusted or selected to enable some flexibility of the primary electrode 704 along the seams 712 between brick segments 710. For example, as shown in FIG. 7B, the two brick segments 710 can pivot relative to each other in one dimension (e.g., one degree of freedom) along the nested interface. The flexible characteristic of the primary electrode 704 may beneficially allow the primary electrode 704 to follow a contour of the implant patient's body structure, such as along the contour of the sternum. If a parasternal electrode is not sufficiently flexible, the air-filled voids between the lead and the body structure may form during the implant process, which is undesirable. Furthermore, a straight or rigid parasternal electrode that is not able to follow the body contour may cause visible protrusions along the skin, which may be uncomfortable and/or may provoke body dysmorphia issues.

The lead 702 may include a distal sensing electrode 720 and a proximal sensing electrode 722. The primary electrode 704 may be disposed between the distal and proximal sensing electrodes 720, 722 along the length of the lead 702.

The sensing electrodes 720, 722 may collect subcutaneous CA signals in connection with multiple cardiac beats. Each of the sensing electrodes 720, 722 may be secured to the adjacent brick segment 710 next to the respective electrode 720, 722. For example, the sensing electrodes 720, 722 may be chemically bonded to the corresponding brick segments 710 via an epoxy or the like. The sensing electrodes 720, 722 may be electrically insulated from the brick segments 710. The lead 702 may include more or less than two sensing electrodes in an alternative embodiment.

The lead 702 includes a lead body 724 that may extend at least most of the length of the lead 702 from the pulse generator 105 (shown in FIG. 1) to a distal end 726 of the lead 702. The segment of the lead body 724 between the primary electrode 704 and the secondary electrode 706 is a gap segment 728, which is referred to herein as a boot 728. In the illustrated embodiment, the lead 702 is a right angle or L-shaped lead 702, and the boot 728 forms the angled corner. The lead body 724 may be composed of an electrically insulative (e.g., dielectric) material. The insulative material may include silicone rubber, polyurethane, and/or the like. The lead body 724 may be formed by molding (e.g., over-molding, injection molding, etc.) the insulative material. In an embodiment, the insulative material is molded over the cables 718 and one or more electrical wires 730 that connect to the sensing electrodes 720, 722. The insulative material may be molded over a portion of the proximal sensing electrode 722 to mechanically secure the primary electrode 704 to the lead body 724 as the insulative material hardens/solidifies. Optionally, the lead body 724 may be at least partially translucent such that the cables 718 and wires 730 within the boot 728 are visible through the insulative material. Optionally, the boot 728 may define one or more suture openings 738 for receiving a suture to tether the boot 728 to tissue during the implant procedure.

The brick segments 710 may be composed of one or more electrically conductive materials that are safe for human tissue interaction. In an embodiment, the brick segments 710 include one or more metals, such as titanium, nickel, chromium, cobalt, stainless steel, and/or the like. The brick segments 710 of the primary electrode 704 may deliver shock therapy to the patient.

FIG. 7C shows a cross-section of one brick segment 710 along line 7C-7C. The brick segment 710 has an oblong cross-sectional shape. The major dimension may be at least 10 F. Optionally, the minor dimension is at least 10 F. The aspect ratio of the major dimension to the minor dimension may be at least 2:1. The other brick segments 710 in the primary electrode 704 may have the same or a similar construction as the illustrated brick segment 710. The brick segment 710 defines multiple bores therethrough. For example, the brick segment 710 may have one or more cable openings 732 for receiving the cable(s) 718 and one or more wire openings 734 for receiving electrical current-carrying wire(s). In an embodiment, the brick segment 710 also includes a cavity 736 for accommodating an implant tool and/or a flushing solution. The cable(s) 718 and the wire(s) 730 are not shown in FIG. 7C or FIG. 7D.

Optionally, the brick segments 710 may have a non-planar surface texture 740. The non-planar surface texture 740 may include non-planar features, such as ridges, protrusions, undulations, saw teeth, dents, depressions, and/or the like. The features may allow the patient tissue to grow into and grip the features, which secures the electrode 704 in place within the patient, reducing the likelihood of lead migration from the implant position.

Figure 8:
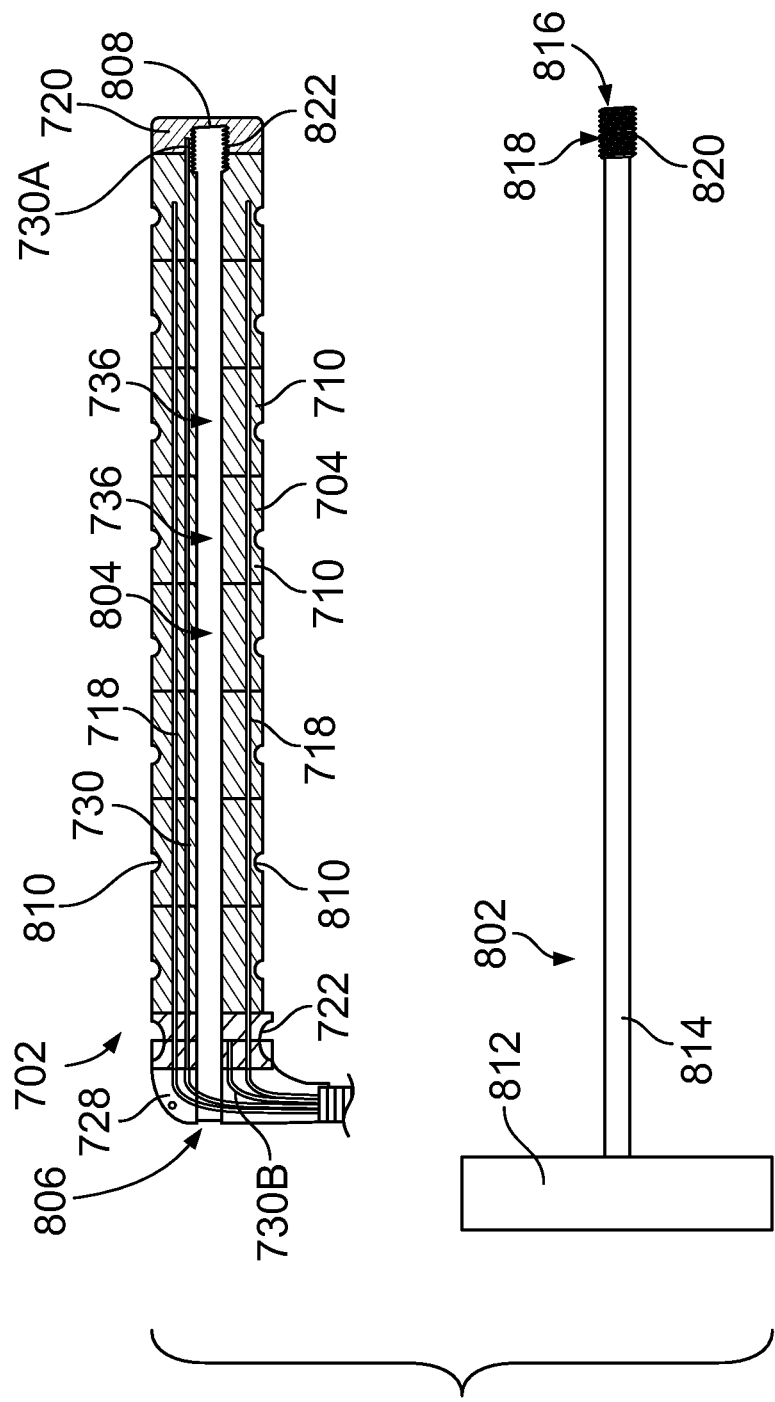
FIG. 8 is a cross-sectional view of a portion of the lead and a plan view of an implant tool according to an embodiment.

FIG. 8 is a cross-sectional view of a portion of the lead 702 and a plan view of an implant tool 802 according to an embodiment. The illustrated portion of the lead 702 includes the sensing electrodes 720, 722, the primary shocking electrode 704, and the boot 728. The cross-section is taken along line 8-8 in FIG. 7B. The lead 702 in the illustrated embodiment has a lumen 804 defined in part by the cavities 736 of the brick segments 710. The lumen 804 continuously extends from an inlet 806 in the boot 728 through the proximal sensing electrode 722, then the brick segments 710, to the distal sensing electrode 720. The distal sensing electrode 720 may include a closed end 808 of the lumen 804. Alternatively, the lumen 804 may extend through a full length of the sensing electrode 720, such that the electrode 720 defines an outlet.

The cables 718 extend through the brick segments 710 to mechanically tether the brick segments 710 together in line. In the illustrated embodiment, two cables 718 are used, and the cables 718 are disposed on opposite sides of the lumen 804. In an embodiment, the cables 718 may be mechanically coupled (e.g., locked) to the brick segments 710 by crimping the brick segments 710 onto the cables 718. For example, each brick segment 710 may be crimped with the cables 718 inside, and the crimp forces may form depressed features 810 in the brick segment bodies. In another embodiment, the cables 718 may be secured (e.g., locked) to the distal-most brick segment 710 that is bonded to the distal sensing electrode 720 and/or to the distal sensing electrode 720 itself, without being secured to one or more of the other brick segments 710. For example, the cables 718 may be secured within the boot 728 in a way that the cables 718 are under tension between the distal brick segment 710 and the boot 728, and the tension maintains the positioning of the brick segments 710. In an alternative embodiment, the same wire and/or cable may be used to convey electric current and provide mechanical retention of the brick segments 710, rather than having two separate elements. For example, the electrical wires 730 that electrically connect to one or more of the electrodes 720, 722, and/or 704 may be used to mechanically couple the brick segments 710 together, such that the lead 702 omits the cables 718.

FIG. 8 shows one electrical wire 730A that extends through the brick segments 710 to the distal sensing electrode 720. A second electrical wire 730B terminates at the proximal sensing electrode 722 without extending through the brick segments 710. The electrical wires 730A, 730B may be insulated wires for electrical insulation from other electrically conductive components, such as the brick segments 710. The lead 702 may include more or less than two electrical wires 730 in other embodiments. For example, the lead 702 may include one or more additional electrical wires 730 that electrically connect to the brick segments 710 for conveying electrical current to power shocking pulses of the primary electrode 704.

In an embodiment, the lead 702 is designed to enable blunt dissection through patient tissue during implant. For example, in contrast to the implant procedure that uses the implant tool assembly 300 shown in FIGS. 3 and 4, the lead 702 may not need to be inserted through a pre-implanted sheath. The lead 702 may be self-implanting. In one example self-implanting application, the lead 702 may not even need a pre-formed channel through the patient formed via a tunneling tool. For example, the lead 702 may be sufficiently rigid and stiff with the implant tool 802 inserted in the lumen 804 that the lead 702 can blunt dissect and form the channel through the patient. The distal sensing electrode 720 may have a tapered shape at the distal end 726 of the lead 702 to carve through the tissue. For example, the electrode 720 may have a bullet-like shape as shown in the side view of FIG. 7B. The tapered shape enables blunt dissection with less input force and less damage to the tissue than if the distal end 726 has a shape that is more blunt. The lead 702 itself may represent a tunneling tool that creates the channel, obviating the need to create a channel prior to lead insertion. In another example self-implanting application, a discrete tunneling tool may be used first to form the channel through the patient tissue, and then the tunneling tool may be extracted before the lead 702 is inserted into the channel using the implant tool 802.

Furthermore, to increase the rigidity of the lead 702 for the blunt dissection, the implant tool 802 is designed to be inserted through the lumen 804. The implant tool 802 has a handle 812 and a rod 814 or pole that extends from the handle 812 to a distal end 816 of the rod 814. The rod 814 is linear and is sized to fit within the lumen 804. The implant tool 802 may be rigid. For example, the implant tool 802 may include one or more metals. In an embodiment, to implant the lead 702, the rod 814 of the implant tool 802 is inserted into the lumen 804 through the inlet 806 in the boot 728. The rod 814 traverses through all or at least most of the brick segments 710. With the rod 814 extending through the brick segments 710 the primary electrode 704 is relatively rigid, such that the amount that the brick segments 710 are permitted to pivot relative to one another is substantially limited and the primary electrode is substantially linear. During the implant procedure, the operator uses the handle 812 to manipulate the lead 702 into a desired implant position within the channel of the patient. Once in place, the operator extracts the implant tool 802 from the lead 702 by pulling the tool 802 such that the rod 814 exits the lumen 804. The lead 702 is left in place, and the incision in the patient is closed.

In an embodiment, a distal tip 818 of the rod 814 may include a securing feature 820 for removably coupling to the distal sensing electrode 720 and/or the distal-most brick segment 710. For example, the securing feature 820 may include helical threads that can couple to complementary threads 822 near the end 808 of the lumen 804. The coupling between the rod 814 and the lead 702 can be useful, particularly for extracting the lead 702 from the patient if necessary.

Referring now back to FIGS. 7A and 7D with continued reference to FIG. 8, the lead 702 may include flushing holes 750 that are fluidly connected to the lumen 804. The flushing holes 750 may emit a flushing fluid, such as a saline solution, into the internal cavity of the patient to wet the outer surfaces of the lead 702. In the illustrated embodiment, the brick segments 710 define the flushing holes 750. The flushing holes 750 connect to the cavities 736 of the brick segments 710. In an embodiment, the internal cavity of the patient may be flushed by injecting the flushing fluid into the lumen 804 through the inlet 806, such as via a syringe. The fluid is emitted or secreted from the lead 702 at different locations along the length of the lead 702 via the flushing holes 750. Some of the fluid may be emitted at the seams 712 between the brick segments 710. Ejecting the fluid at different locations and directions from the lead 702 may provide more reliable, effective, and/or cleaner establishment of the fluid-electrode interface without air bubbles. It is noted that the lead 702 itself in this embodiment functions similar to the sheath 304 described in FIGS. 3 and 4, such that a discrete flushing sheath is not needed. In an alternative embodiment, the lead 702 does not include the flushing holes 750 because the seams 712 may function as flushing holes. For example, a sufficient amount of saline solution or other fluid injected into the lumen 804 may be emitted from the lead 702 at different locations along the length via the seams 712, so discrete flushing holes 750 are unnecessary.

In an alternative embodiment, the lead 702 is not self-implantable via blunt dissection. For example, the lead 702 does not include the lumen 804, and the brick segments 710 of the primary shocking electrode 704 do not include the cavities 736. In this alternative embodiment, the lead 702 with the segmented primary shocking electrode 704 may be implanted via the implant tool assembly 300 shown in FIGS. 3 and 4, or a similar tool assembly.

In the illustrated embodiment, the primary shocking electrode 704 is segmented into brick segments 710, and the secondary shocking electrode 706 is not segmented. In another embodiment, the secondary shocking electrode 706 is segmented into brick segments and has a similar construction as the primary shocking electrode 704. Optionally, the secondary shocking electrode 706 may be shorter in length than the primary shocking electrode 704, such as with fewer brick segments or smaller brick segments than the primary electrode 704.

Figure 9B:
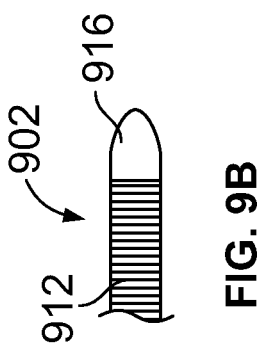
FIG. 9B is a side view of a distal portion of the lead shown in FIG. 9A.
Figure 9C:
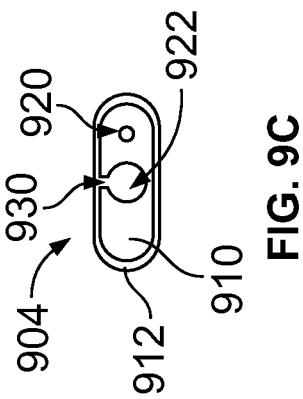
FIG. 9C illustrates a cross-sectional shape of a primary shocking electrode taken along line 9C-9C in FIG. 9A.
Figure 9A:
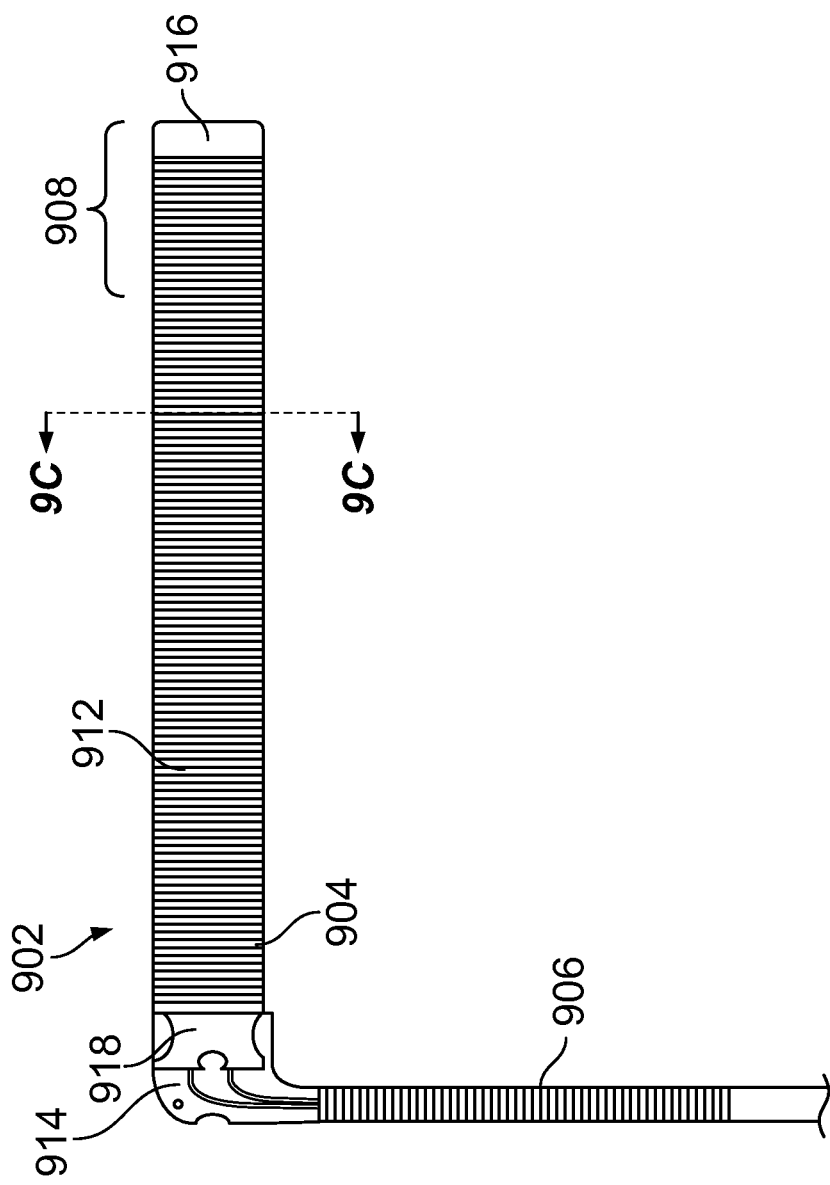
FIG. 9A illustrates a plan view of a lead according to an embodiment.

FIG. 9A illustrates a plan view of a lead 902 according to an embodiment. The lead 902 may be the lead 120 shown in FIG. 1. The lead 902 includes a primary shocking electrode 904 and a secondary shocking electrode 906. FIG. 9B is a side view of a distal portion 908 of the lead 902 shown in FIG. 9A. FIG. 9C illustrates a cross-sectional shape of the primary electrode 904 taken along line 9C-9C in FIG. 9A. The primary shocking electrode 904 and the secondary shocking electrode 906 optionally may represent the primary shocking electrode 126 and the secondary shocking electrode 128, respectively. For example, the primary electrode 904 may have an oblong cross-sectional shape, as shown in FIG. 9C.

The lead 902 in FIGS. 9A-C differs from the lead 702 in the construction of the primary shocking electrode 904. For example, the primary electrode 904 is not segmented into multiple electrically conductive brick segments. Rather, the primary electrode 904 includes an electrically insulative (e.g., dielectric) base 910 and a coiled wire 912 that surrounds the base 910. The base 910 may be composed of silicone rubber, polyurethane, and/or the like. The base 910 may be sufficiently flexible to enable the primary shocking electrode 904 to confirm to the contour of the patient's body. Optionally, the base 910 may have the same or similar compositions as a lead body 914 of the lead 902. The coiled wire 912 may be an electrically conductive metal that is wound and/or wrapped around the base 910, between a distal sensing electrode 916 and a proximal sensing electrode 918. The sensing electrodes 916, 918 optionally may be the same as the electrodes 720, 722 shown in FIGS. 7A, 7B, and 8. In an embodiment, the base 910 is unitary and extends the entire length of the primary electrode 904 between the sensing electrodes 916, 918. In an alternative embodiment, the electrically insulative base 910 may be segmented into multiple discrete brick segments. The brick segments may be similar in shape as the brick segments 710, although different in material composition. The brick segments may be coupled together via one or more wires or cables, as described above.

In an embodiment, the base 910 defines one or more wire openings 920 for receiving electrical wire(s) therethrough. The base 910 may define a lumen 922 for receiving flushing fluid and/or the rod 814 of the implant tool 802 shown in FIG. 8. For example, the lead 902 may be self-implantable via blunt dissection. The implant tool 802 may be used to implant the lead 902 in the same or a similar fashion as the implantation of the lead 702 described above with reference to FIG. 8. Optionally, the base 910 defines a plurality of flushing holes 930 for emitting flushing fluid, such as a saline solution. One flushing hole 930 is shown in FIG. 9C. The flushing holes 930 are fluidly connected to the lumen 922. The flushing holes 930 may be used to wet the interface between the base 910 and the coiled wire 912 and/or wet the lead-tissue interface.

Figure 10:
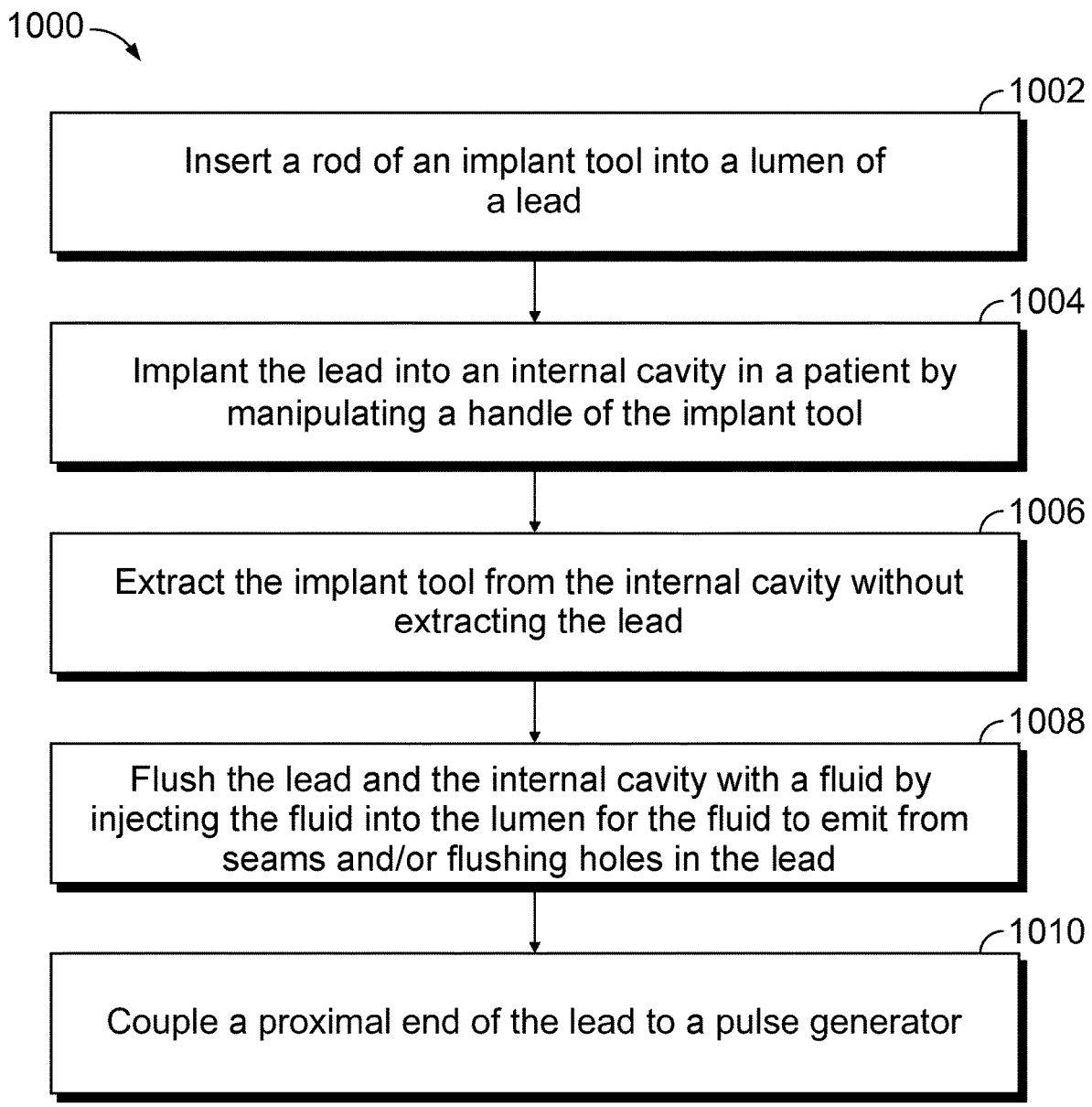
FIG. 10 is a flow chart of a method for implanting a subcutaneous lead of an IMD according to an embodiment.

FIG. 10 is a flow chart 1000 of a method for implanting a subcutaneous lead of an IMD according to an embodiment. The method may include additional steps than shown in FIG. 10, fewer steps than shown in FIG. 10, and/or different steps than shown in FIG. 10. The method may be performed with one of the leads 702 and 902 shown in FIGS. 7A and 9A, respectively. At step 1002, a rod 814 of an implant tool 802 is inserted into a lumen 804, 922 of a lead 702, 902. The lumen 804, 922 extends through a primary shocking electrode 704, 904 of the lead 702, 902.

At step 1004, the lead 702, 902 is implanted into an internal cavity in a patient through an incision by manipulating the implant tool 802. The lead 702, 902 is designed with a tapered distal end to perform blunt dissection of patient tissue during the implant process. An operator, such as a human or a robot, may grasp a handle 812 of the implant tool 802 to load the lead 702, 902, with the rod 814 therein, into the patient internal cavity.

At step 1006, the implant tool 802 is extracted from the internal cavity of the patient without the lead 702, 902, such that the lead 702, 902 remains implanted. For example, the rod 814 may be pulled out from the lumen 804, 922 via the handle 812. In an embodiment, the steps described above are used to implant a distal segment of the lead 702, 902, such as along a parasternal area of the patient. The same steps may be repeated to implant a proximal segment of the lead 702, 902, which includes a secondary electrode 706. For example, the rod 814 of the implant tool 802 may be inserted into a lumen of the secondary electrode 706 to insert the proximal segment into the patient. The proximal segment may be a transverse portion of the lead 702, 902.

At step 1008, the lead 702, 902 and patient internal cavity may be flushed with a fluid, such as saline, by injecting the fluid into the lumen 804, 922. The fluid may be ejected at different locations along the length of the shocking electrode 704, 904 through flushing holes 750, 950 and/or through seams 712 between brick segments 710 of the electrode 704. The proximal segment of the lead 702, 902 may be flushed as well.

At step 1010, a proximal end of the lead 702, 902 may be mechanically coupled and electrically connected to a pulse generator 105 to render the IMD operable.

Closing

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the figures, which illustrate example methods, devices and program products according to various example embodiments. The program instructions may be provided to a processor of a general-purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally, or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. An implantable medical device (IMD) comprising:
a lead configured to be operably coupled to a pulse generator and subcutaneously implanted within a patient, the lead including first electrode and a second electrode configured to receive electrical power from the pulse generator and to deliver high-voltage shocks for defibrillation therapy, wherein the first electrode has a first oblong cross-sectional shape with a major dimension that is at least 10 French (F), the first oblong cross-sectional shape being a rectangle with rounded corners,
wherein the first electrode is configured to be located in a parasternal area of the patient, the second electrode is configured to provide the high-voltage shocks for the defibrillation therapy, the second electrode is disposed between the first electrode and the pulse generator along a length of the lead, the second electrode having a second oblong cross-sectional shape that is different from the first oblong cross-sectional shape of the first electrode.

2. The IMD of claim 1, wherein the first oblong cross-sectional shape of the first electrode has a minor dimension that is less than the major dimension and oriented perpendicular to the major dimension.

3. The IMD of claim 2, wherein an aspect ratio of the major dimension to the minor dimension is at least 2:1.

4. The IMD of claim 2, wherein the minor dimension is at least 10 F and the major dimension is greater than 10 F.

5. The IMD of claim 1, wherein the first oblong cross-sectional shape of the first electrode has first and second planar sides that are parallel to each other and third and fourth planar sides that are parallel to each other, each of the first and second planar sides connected with each of the third and fourth planar sides by the rounded corners.

6. The IMD of claim 1, wherein the first electrode has a first orientation extending from a proximal end of the first electrode to a distal end of the first electrode, and the second electrode has a second orientation extending from a proximal end of the second electrode to a distal end of the second electrode, wherein the first orientation is transverse to the second orientation.

7. The IMD of claim 1, wherein the first electrode comprises a plurality of electrically conductive brick segments that are coupled together in a line.

8. The IMD of claim 1, further comprising the pulse generator, wherein the pulse generator is configured to supply the electrical power at less than 1000 V through the lead to the second electrode to provide the high-voltage shocks.

9. The IMD of claim 1, further comprising the pulse generator, wherein the pulse generator has a volume less than 50 $cm^3$.

10. The IMD of claim 1, wherein the first electrode is longer than the second electrode.

11. The IMD of claim 1, wherein the first electrode and the second electrode are spaced apart from each other along a length of the lead by a gap segment adapted to be positioned at a xiphoid process of the patient.

12. The IMD of claim 1, wherein the first electrode is adapted to be positioned along an anterior region of a chest of the patient and the second electrode laterally extends between the primary electrode and the pulse generator.

13. The IMD of claim 1, wherein the first electrode is adapted to be oriented parallel to a midsternal line of the patient while implanted in the patient, and the second electrode is oriented at an angle between sixty degrees and one hundred twenty degrees to the first electrode.

14. A method of producing an implantable medical device (IMD), the method comprising:
- forming a lead that is configured to be operably coupled to a pulse generator and subcutaneously implanted within a patient; and
- securing first and second electrodes on the lead, the first and second electrodes configured to receive electrical power from the pulse generator and to deliver high-voltage shocks for defibrillation therapy, wherein the first electrode has a first oblong cross-sectional shape with a major dimension that is at least 10 French (F), the first oblong cross-sectional shape being a rectangle with rounded corners, the first electrode secured on the lead to be located in a parasternal area of the patient, the second electrode secured on the lead to be located between the first electrode and the pulse generator along a length of the lead, the second electrode having a second oblong cross-sectional shape that is different from the first oblong cross-sectional shape of the first electrode.

15. The method of claim 14, wherein the first oblong cross-sectional shape of the first electrode has a minor dimension that is less than the major dimension and is perpendicular to the major dimension, and an aspect ratio of the major dimension to the minor dimension is at least 2:1.

16. The method of claim 14, further comprising implanting the lead such that the first electrode has a first orientation extending from a proximal end of the first electrode to a distal end of the first electrode, and the second electrode has a second orientation extending from a proximal end of the second electrode to a distal end of the second electrode, wherein the first orientation is transverse to the second orientation.

17. The method of claim 14, wherein the first electrode and the second electrode are secured on the lead with the first electrode and the second electrode spaced apart from each other along a length of the lead by a gap segment positioned at a xiphoid process of the patient.

18. The method of claim 14, wherein the first electrode and the second electrode are secured on the lead with the first electrode is positioned along an anterior region of a chest of the patient and the second electrode laterally extending between the primary electrode and the pulse generator.

19. The method of claim 14, wherein the first electrode and the second electrode are secured on the lead with the first electrode oriented parallel to a midsternal line of the patient while implanted in the patient and the second electrode oriented at an angle between sixty degrees and one hundred twenty degrees to the first electrode.

* * * * *